United States Patent
Gentz et al.

(10) Patent No.: US 6,548,262 B2
(45) Date of Patent: Apr. 15, 2003

(54) METHODS OF MEASURING TISSUE FACTOR PATHWAY INHIBITOR-3

(75) Inventors: Reiner L. Gentz, Silver Spring, MD (US); Tsu-An Hsu, Harleysville, PA (US); Craig A. Rosen, Laytonsville; Jian Ni, Rockville, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 9 days.

(21) Appl. No.: 09/827,948

(22) Filed: Apr. 6, 2001

(65) Prior Publication Data

US 2001/0029034 A1 Oct. 11, 2001

Related U.S. Application Data

(62) Division of application No. 09/013,896, filed on Jan. 27, 1998, now Pat. No. 6,262,233.
(60) Provisional application No. 60/036,703, filed on Jan. 31, 1997.

(51) Int. Cl.$^7$ .................. G01N 33/50; G01N 33/48
(52) U.S. Cl. .................. 435/7.1; 435/7.5; 435/7.6; 435/7.7; 435/7.9; 435/40.5; 435/69.1
(58) Field of Search .................. 435/7.1, 7.5, 7.6, 435/7.7, 7.9, 40.5, 69.1

(56) References Cited

U.S. PATENT DOCUMENTS

| | | | |
|---|---|---|---|
| 5,731,412 A | 3/1998 | Shimomura et al. | 530/350 |
| 5,854,396 A | 12/1998 | Shimomura et al. | 530/350 |
| 6,262,233 B1 | 7/2001 | Gentz et al. | 530/350 |

FOREIGN PATENT DOCUMENTS

| | | |
|---|---|---|
| EP | 0 758 682 | 2/1997 |
| WO | WO 96/20278 | 7/1996 |
| WO | WO 97/33996 | 9/1997 |

OTHER PUBLICATIONS

Geneseq Database, Report No. T23829, from Matsubara, K., et al., as disclosed in WO 95/14772, published Jun. 1, 1995.
Geneseq Database, Report No. T61439, from Dawaguchi, T., et al., as disclosed in EP 758682, published Feb. 19, 1997.
Geneseq Database, Report No. T90731, from Davis, G., et al., as disclosed in WO 97/33996, published Sep. 18, 1997.
Geneseq Database, Report No. T90732, from Davis, G., et al., as disclosed in WO 97/33996, published Sep. 18, 1997.
Geneseq Database, Report No. T90733, from David G., et al., as disclosed in WO 97/33996, published Sep. 18, 1997.
Geneseq Database, Report No. T90734, from Davis, G., et al., as disclosed in WO 97/33996, published Sep. 18, 1997.
Geneseq Database, Report No. T90735, from Davis, G., et al., as disclosed in WO 97/33996, published Sep. 18, 1997.
Geneseq Database, Report No. T90736, from Davis, G., et al., as disclosed in WO 97/33996, published Sep. 18, 1997.
Geneseq Database, Report No. V33063, from Gentz, R.L., et al., as disclosed in WO 98/33920, published Aug. 6, 1998.
NCBI Entrez, GenBank Report, Accession No. R35464, from Hillier, L., et al. (May 1995).
NCGI Entrez, GenBank Report, Accession No. R74593, from Hillier, L., et al. (Jun. 1995).
NCBI Entrez, GenBank Report, Accession No. N30199, from Hillier, L., et al. (Jan. 1996).
NCBI Entrez, GenBank Report, Accession No. N39798, from Hillier, L., et al. (Jan. 1996).
NCBI Entrez, GenBank Report, Accession No. W68848, from Hillier, L., et al. (Jun. 1996).
NCBI Entrez, GenBank Report, Accession No. W96472, from Hillier, L., et al. (Jul. 1996).
NCBI Entrez, GenBank Report, Accession No. Z36849, from Mueller–Pillasch, F., et al. (Apr. 1997).
NCBI Entrez, GenBank Report, Accession No. W89123, from Hillier, L., et al. (May 1997).
NCBI Entrez, GenBank Report, Accession No. AA031287, from Hillier, L., et al. (May 1997).

*Primary Examiner*—Elizabeth Kemmerer
(74) *Attorney, Agent, or Firm*—Sterne, Kessler, Goldstein & Fox P.L.L.C.

(57) ABSTRACT

The present invention relates to a novel TFPI-3 protein which is a member of the tissue factor protease inhibitor family. In particular, isolated nucleic acid molecules are provided encoding human TFPI-3 proteins. TFPI-3 polypeptides are also provided as are vectors, host cells and recombinant methods for producing the same. The invention further relates to screening methods for identifying agonists and antagonists of TFPI-3 activity. Also provided are diagnostic methods for detecting hemostasis system-related disorders and therapeutic methods for treating hemostatis system-related disorders.

32 Claims, 5 Drawing Sheets

```
CTGCCCGGCCACCTTCGGGAGCCGCTTCCAATAGGCGTTCGCCATTGGCTCTGGCGACCT

CCGCGCGTTGGGAGGTGTAGCGCGGCTCTGAACGCGCTGAGGGCCGTTGAGTGTCGCAGG

CGGCGAGGGCGCGAGTGAGGAGCAGACCCAGGCATCGCGCGCCGAGAAGGCCGGGCGTCC

CCACACTGAAGGTCCGGAAAGGCGACTTCCGGGGGCTTTGGCACCTGGCGGACCCTCCCG

GAGCGTCGGCACCTGAACGCGAGGCGCTCCATTGCGCGTGCGCGTTGAGGGGCTTCCCGC

ACCTGATCGCGAGACCCCAACGGCTGGTGGCGTCGCCTGCGCGTCTCGGCTGAGCTGGCC

ATGGCGCAGCTGTGCGGGCTGAGGCGGAGCCGGGCGTTTCTCGCCCTGCTGGGATCGCTG
 M  A  Q  L  C  G  L  R  R  S  R  A  F  L  A  L  L  G  S  L

CTCCTCTCTGGGGTCCTGGCGGCCGACCGAGAACGCAGCATCCACGACTTCTGCCTGGTG
 L  L  S  G  V  L  A  A  D  R  E  R  S  I  H  D  F  C  L  V
                        ********

TCGAAGGTGGTGGGCAGATGCCGGGCCTCCATGCCTAGGTGGTGGTACAATGTCACTGAC
 S  K  V  V  G  R  C  R  A  S  M  P  R  W  W  Y  N  V  T  D
 ************************************************************

GGATCCTGCCAGCTGTTTGTGTATGGGGGCTGTGACGGAAACAGCAATAATTACCTGACC
 G  S  C  Q  L  F  V  Y  G  G  C  D  G  N  S  N  N  Y  L  T
 ************************************************************

AAGGAGGAGTGCCTCAAGAAATGTGCCACTGTCACAGAGAATGCCACGGGTGACCTGGCC
 R  E  E  C  L  K  K  C  A  T  V  T  E  N  A  T  G  D  L  A
 **********************

ACCAGCAGGAATGCAGCGGATTCCTCTGTCCCAAGTGCTCCCAGAAGGCAGGATTCTGAA
 T  S  R  N  A  A  D  S  S  V  P  S  A  P  R  R  Q  D  S  E

GACCACTCCAGCGATATGTTCAACTATGAAGAATACTGCACCGCCAACGCAGTCACTGGG
 D  H  S  S  D  M  F  N  Y  E  E  Y  C  T  A  N  A  V  T  G
                            ************************

CCTTGCCGTGCATCCTTCCCACGCTGGTACTTTGACGTGGAGAGGAACTCCTGCAATAAC
 P  C  R  A  S  F  P  R  W  Y  F  D  V  E  R  N  S  C  N  N
 * * * * * * * * * * * * * * * * * * * * * * * * * * * * * *

TTCATCTATGGAGGCTGCCGGGGGCAATAAGAACAGCTACCGCTCTGAGGAGGCCTGCATG
 F  I  Y  G  G  C  R  G  N  K  N  S  Y  R  S  E  E  A  C  M
 * * * * * * * * * * * * * * * * * * * * * * * * * *

CTCCGCTGCTTCCGCCAGCAGGAGAATCCTCCCCTGCCCCTTGGCTCAAAGGTGGTGGTT
 L  R  C  F  R  Q  Q  E  N  P  P  L  P  L  G  S  K  V  V  V
 ******
```

FIG.1A

CTGGCGGGGCTGTTCGTGATGGTGTTGATCCTCTTCCTGGGAGCCTCCATGGTCTACCTG
L  A  G  L  F  V  M  V  L  I  L  F  L  G  A  S  M  V  Y  L

ATCCGGGTGGCACGGAGGAACCAGGAGCGTGCCCTGCGCACCGTCTGGAGCTCCGGAGAT
I  R  V  A  R  R  N  Q  E  R  A  L  R  T  V  W  S  S  G  D

GACAAGGAGCAGCTGGTGAAGAACACATATGTCCTGTGACCGCCCTGTCGCCAAGAGGAC
D  K  E  Q  L  V  K  N  T  Y  V  L  *

TGGGGAAGGGAGGGGAGACTATGTGTGAGCTTTTTTTAAATAGAGGGATTGACTCGGATT

TGAGTGATCATTAGGGCTGAGGTCTGTTTCTCTGGGAGGTAGGACGGCTGCTTCCTGGTC

TGGCAGGGATGGGTTTGCTTTGGAAATCCTCTAGGAGGCTCCTCCTCGCATGGCCTGCAG

TCTGGCAGCAGCCCCGAGTTGTTTCCTCGCTGATCGATTTCTTTCCTCCAGGTAGAGTTT

TCTTTGCTTATGTTGAATTCCATTGCCTCTTTTCTCATCACAGAAGTGATGTTGGAATCG

TTTCTTTTGTTTGTCTGATTTATGGTTTTTTTAAGTATAAACAAAAGTTTTTTATTAGCA

TTCTGAAAGAAGGAAAGTAAAATGTACAAGTTTAATAAAAAGGGGCCTTCCCCTTTAGAA

TAAATTTCAGCATGTGCTTTCAAAAAAAAAAAAAAAAAAAAAAAAAAAAA

FIG. 1B

```
       -----CLLPADTGPCRASITRYFYNVXTGS    Majority
             |              |              |
             10             20             30
             |              |              |
 1   RRPDF CLEPPYTGPCKARIIRYFYNAKAGL       APROTININ
 1   ----- CAFKADDGPCKAIMKRFFNIFTHQ        TFPI-1 KUNTIZ-1
 1   ----- CFLEEDPGICHGYITRYFYNNQTKQ       TFPI-1 KUNITZ-2
 1   ----- CLTPADRGLCRANENRFYYNSVIGK       TFPI-1 KUNITZ-3
 1   ----- CLLPLDYGPCRALLLRYYYDRYTQS       TFPI-2 KUNITZ-1
 1   CR--- LQVSVDDQCEGSTEKYFFNLSSMT        TFPI-2 KUNITZ-1
 1   ----- CYSPKDEGLCSANVTRYYFNPRYRT       TFPI-2 KUNITZ-3
 1   ----- CLVSKVVGRCRASMPRWWYNVTDGS       TFPI-3 KUNITZ-1
 1   ----- CTANAVTGPCRASFPRWYFDVERNS       TFPI-3 KUNITZ-2

CEXFVYGGCGGNR--NNFESLEECKRAC--        Majority
             |              |              |
             40             50             60
             |              |              |
31   CQTFVYGGCRAKR--NNFKSAEDCMRTCGG        APROTININ
26   CEEFIYGGCEGNQ--NRFESLEECKKMC          TFPI-1 JUNTIZ-1
26   CERFKYGGCLGNM--NNFETLEECKNIC          TFPI-1 JUNITZ-2
26   CRPFKYSGCGGNE--NNFTSKQECLRAC          TFPI-1 KUNITZ-3
26   CRQFLYGGCEGNA--NNFYTWEACDDAC          TFPI-2 KUNITZ-1
27   CEKFFSGGCHRNRIENRFPDEATCMGFC          TFPI-2 KUNITZ-2
26   CDAFTYTGCGGND--NNFVSREDCKRAC          TFPI-2 KUNITZ-3
26   CQLFVYGGCDGNS--NNYLTKEECLKKC          TFPI-3 KUNITZ-1
26   CNNFIYGGCRGNK--NSYRSEEACMLRC          TFPI-3 KUNITZ-2

-                                    Majority

59    A                                    APROTININ
51                                         TFPI-1 JUNTIZ-1
51                                         TFPI-1 JUNITZ-2
51                                         TFPI-1 KUNITZ-3
51                                         TFPI-2 KUNITZ-1
54                                         TFPI-2 KUNITZ-2
51                                         TFPI-2 KUNITZ-3
51                                         TFPI-3 KUNITZ-1
51                                         TFPI-3 KUNITZ-2
```

FIG.2

SEQUENCE LISTING

<160> NUMBER OF SEQ ID NOS: 31

<210> SEQ ID NO 1
<211> LENGTH: 1610
<212> TYPE: DNA
<213> ORGANISM: Homo sapiens
<220> FEATURE:
<221> NAME/KEY: CDS
<222> LOCATION: (361)..(1116)
<221> NAME/KEY: sig_peptide
<222> LOCATION: (361)..(439)
<221> NAME/KEY: mat_peptide
<222> LOCATION: (442)..(1116)

<400> SEQUENCE: 1

-continued

```
ctgcccggcc accttcggga gccgcttcca ataggcgttc gccattggct ctggcgacct      60
ccgcgcgttg ggaggtgtag cgcggctctg aacgcgctga gggccgttga gtgtcgcagg     120
cggcgagggc gcgagtgagg agcagaccca ggcatcgcgc gccgagaagg ccgggcgtcc     180
ccacactgaa ggtccggaaa ggcgacttcc ggggctttg gcacctggcg gaccctcccg      240
gagcgtcggc acctgaacgc gaggcgctcc attgcgcgtg cgcgttgagg ggcttcccgc     300
acctgatcgc gagaccccaa cggctggtgg cgtcgcctgc gcgtctcggc tgagctggcc     360
```

| | | | | | | | | | | | | | | | | |
|---|---|---|---|---|---|---|---|---|---|---|---|---|---|---|---|---|
| atg | gcg | cag | ctg | tgc | ggg | ctg | agg | cgg | agc | cgg | gcg | ttt | ctc | gcc | ctg | 408 |
| Met | Ala | Gln | Leu | Cys | Gly | Leu | Arg | Arg | Ser | Arg | Ala | Phe | Leu | Ala | Leu | |
| | -25 | | | | -20 | | | | | -15 | | | | | | |
| ctg | gga | tcg | ctg | ctc | ctc | tct | ggg | gtc | ctg | gcg | gcc | gac | cga | gaa | cgc | 456 |
| Leu | Gly | Ser | Leu | Leu | Leu | Ser | Gly | Val | Leu | Ala | Ala | Asp | Arg | Glu | Arg | |
| -10 | | | | | -5 | | | | | -1 | 1 | | | 5 | | |
| agc | atc | cac | gac | ttc | tgc | ctg | gtg | tcg | aag | gtg | gtg | ggc | aga | tgc | cgg | 504 |
| Ser | Ile | His | Asp | Phe | Cys | Leu | Val | Ser | Lys | Val | Val | Gly | Arg | Cys | Arg | |
| | | | 10 | | | | | 15 | | | | | 20 | | | |
| gcc | tcc | atg | cct | agg | tgg | tgg | tac | aat | gtc | act | gac | gga | tcc | tgc | cag | 552 |
| Ala | Ser | Met | Pro | Arg | Trp | Trp | Tyr | Asn | Val | Thr | Asp | Gly | Ser | Cys | Gln | |
| | | 25 | | | | | 30 | | | | | 35 | | | | |
| ctg | ttt | gtg | tat | ggg | ggc | tgt | gac | gga | aac | agc | aat | aat | tac | ctg | acc | 600 |
| Leu | Phe | Val | Tyr | Gly | Gly | Cys | Asp | Gly | Asn | Ser | Asn | Asn | Tyr | Leu | Thr | |
| | 40 | | | | | 45 | | | | | 50 | | | | | |
| aag | gag | gag | tgc | ctc | aag | aaa | tgt | gcc | act | gtc | aca | gag | aat | gcc | acg | 648 |
| Lys | Glu | Glu | Cys | Leu | Lys | Lys | Cys | Ala | Thr | Val | Thr | Glu | Asn | Ala | Thr | |
| 55 | | | | | 60 | | | | | 65 | | | | | | |
| ggt | gac | ctg | gcc | acc | agc | agg | aat | gca | gcg | gat | tcc | tct | gtc | cca | agt | 696 |
| Gly | Asp | Leu | Ala | Thr | Ser | Arg | Asn | Ala | Ala | Asp | Ser | Ser | Val | Pro | Ser | |
| 70 | | | | 75 | | | | | 80 | | | | | 85 | | |
| gct | ccc | aga | agg | cag | gat | tct | gaa | gac | cac | tcc | agc | gat | atg | ttc | aac | 744 |
| Ala | Pro | Arg | Arg | Gln | Asp | Ser | Glu | Asp | His | Ser | Ser | Asp | Met | Phe | Asn | |
| | | | | 90 | | | | | 95 | | | | | 100 | | |
| tat | gaa | gaa | tac | tgc | acc | gcc | aac | gca | gtc | act | ggg | cct | tgc | cgt | gca | 792 |
| Tyr | Glu | Glu | Tyr | Cys | Thr | Ala | Asn | Ala | Val | Thr | Gly | Pro | Cys | Arg | Ala | |
| | | | 105 | | | | | 110 | | | | | 115 | | | |
| tcc | ttc | cca | cgc | tgg | tac | ttt | gac | gtg | gag | agg | aac | tcc | tgc | aat | aac | 840 |
| Ser | Phe | Pro | Arg | Trp | Tyr | Phe | Asp | Val | Glu | Arg | Asn | Ser | Cys | Asn | Asn | |
| | | 120 | | | | | 125 | | | | | 130 | | | | |
| ttc | atc | tat | gga | ggc | tgc | cgg | ggc | aat | aag | aac | agc | tac | cgc | tct | gag | 888 |
| Phe | Ile | Tyr | Gly | Gly | Cys | Arg | Gly | Asn | Lys | Asn | Ser | Tyr | Arg | Ser | Glu | |
| | 135 | | | | | 140 | | | | | 145 | | | | | |
| gag | gcc | tgc | atg | ctc | cgc | tgc | ttc | cgc | cag | cag | gag | aat | cct | ccc | ctg | 936 |
| Glu | Ala | Cys | Met | Leu | Arg | Cys | Phe | Arg | Gln | Gln | Glu | Asn | Pro | Pro | Leu | |
| 150 | | | | 155 | | | | | 160 | | | | | 165 | | |
| ccc | ctt | ggc | tca | aag | gtg | gtg | gtt | ctg | gcg | ggg | ctg | ttc | gtg | atg | gtg | 984 |
| Pro | Leu | Gly | Ser | Lys | Val | Val | Val | Leu | Ala | Gly | Leu | Phe | Val | Met | Val | |
| | | | 170 | | | | | 175 | | | | | 180 | | | |
| ttg | atc | ctc | ttc | ctg | gga | gcc | tcc | atg | gtc | tac | ctg | atc | cgg | gtg | gca | 1032 |
| Leu | Ile | Leu | Phe | Leu | Gly | Ala | Ser | Met | Val | Tyr | Leu | Ile | Arg | Val | Ala | |
| | | 185 | | | | | 190 | | | | | 195 | | | | |
| cgg | agg | aac | cag | gag | cgt | gcc | ctg | cgc | acc | gtc | tgg | agc | tcc | gga | gat | 1080 |
| Arg | Arg | Asn | Gln | Glu | Arg | Ala | Leu | Arg | Thr | Val | Trp | Ser | Ser | Gly | Asp | |
| | 200 | | | | | 205 | | | | | 210 | | | | | |
| gac | aag | gag | cag | ctg | gtg | aag | aac | aca | tat | gtc | ctg | tgaccgccct | | | | 1126 |
| Asp | Lys | Glu | Gln | Leu | Val | Lys | Asn | Thr | Tyr | Val | Leu | | | | | |
| 215 | | | | | 220 | | | | | 225 | | | | | | |

```
gtcgccaaga ggactgggga agggagggga gactatgtgt gagcttttt taaatagagg     1186 gattgactcg gatttgagtg atcattaggg ctgaggtctg tttctctggg aggtaggacg     1246
```

-continued

```
gctgcttcct ggtctggcag ggatgggttt gctttggaaa tcctctagga ggctcctcct      1306
cgcatggcct gcagtctggc agcagccccg agttgtttcc tcgctgatcg atttctttcc      1366
tccaggtaga gttttctttg cttatgttga attccattgc ctcttttctc atcacagaag      1426
tgatgttgga atcgtttctt ttgtttgtct gatttatggt ttttttaagt ataaacaaaa      1486
gttttttatt agcattctga aagaaggaaa gtaaaatgta caagtttaat aaaaaggggc      1546
cttccccttt agaataaatt tcagcatgtg ctttcaaaaa aaaaaaaaaa aaaaaaaaa       1606 aaaa                                                                  1610
```

<210> SEQ ID NO 2
<211> LENGTH: 252
<212> TYPE: PRT
<213> ORGANISM: Homo sapiens

<400> SEQUENCE: 2

```
Met Ala Gln Leu Cys Gly Leu Arg Arg Ser Arg Ala Phe Leu Ala Leu
        -25                 -20                 -15
Leu Gly Ser Leu Leu Leu Ser Gly Val Leu Ala Ala Asp Arg Glu Arg
    -10                  -5              -1   1               5
Ser Ile His Asp Phe Cys Leu Val Ser Lys Val Val Gly Arg Cys Arg
                     10                  15                  20
Ala Ser Met Pro Arg Trp Trp Tyr Asn Val Thr Asp Gly Ser Cys Gln
                 25                  30                  35
Leu Phe Val Tyr Gly Gly Cys Asp Gly Asn Ser Asn Asn Tyr Leu Thr
             40                  45                  50
Lys Glu Glu Cys Leu Lys Lys Cys Ala Thr Val Thr Glu Asn Ala Thr
         55                  60                  65
Gly Asp Leu Ala Thr Ser Arg Asn Ala Ala Asp Ser Ser Val Pro Ser
 70                  75                  80                  85
Ala Pro Arg Arg Gln Asp Ser Glu Asp His Ser Ser Asp Met Phe Asn
                 90                  95                 100
Tyr Glu Glu Tyr Cys Thr Ala Asn Ala Val Thr Gly Pro Cys Arg Ala
             105                 110                 115
Ser Phe Pro Arg Trp Tyr Phe Asp Val Glu Arg Asn Ser Cys Asn Asn
         120                 125                 130
Phe Ile Tyr Gly Gly Cys Arg Gly Asn Lys Asn Ser Tyr Arg Ser Glu
     135                 140                 145
Glu Ala Cys Met Leu Arg Cys Phe Arg Gln Gln Glu Asn Pro Pro Leu
150                 155                 160                 165
Pro Leu Gly Ser Lys Val Val Leu Ala Gly Leu Phe Val Met Val
                 170                 175                 180
Leu Ile Leu Phe Leu Gly Ala Ser Met Val Tyr Leu Ile Arg Val Ala
             185                 190                 195
Arg Arg Asn Gln Glu Arg Ala Leu Arg Thr Val Trp Ser Ser Gly Asp
         200                 205                 210
Asp Lys Glu Gln Leu Val Lys Asn Thr Tyr Val Leu
     215                 220                 225
```

<210> SEQ ID NO 3
<211> LENGTH: 59
<212> TYPE: PRT
<213> ORGANISM: Bovine

<400> SEQUENCE: 3

```
Arg Arg Pro Asp Phe Cys Leu Glu Pro Pro Tyr Thr Gly Pro Cys Lys
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
            35                  40                  45

Ala Glu Asp Cys Met Arg Thr Cys Gly Gly Ala
        50                  55
```

<210> SEQ ID NO 4
<211> LENGTH: 51
<212> TYPE: PRT
<213> ORGANISM: Human

<400> SEQUENCE: 4

```
Cys Ala Phe Lys Ala Asp Asp Gly Pro Cys Lys Ala Ile Met Lys Arg
1               5                   10                  15

Phe Phe Phe Asn Ile Phe Thr His Gln Cys Glu Glu Phe Ile Tyr Gly
            20                  25                  30

Gly Cys Glu Gly Asn Gln Asn Arg Phe Glu Ser Leu Glu Glu Cys Lys
            35                  40                  45

Lys Met Cys
        50
```

<210> SEQ ID NO 5
<211> LENGTH: 51
<212> TYPE: PRT
<213> ORGANISM: Human

<400> SEQUENCE: 5

```
Cys Phe Leu Glu Glu Asp Pro Gly Ile Cys His Gly Tyr Ile Thr Arg
1               5                   10                  15

Tyr Phe Tyr Asn Asn Gln Thr Lys Gln Cys Glu Arg Phe Lys Tyr Gly
            20                  25                  30

Gly Cys Leu Gly Asn Met Asn Asn Phe Glu Thr Leu Glu Glu Cys Lys
            35                  40                  45

Asn Ile Cys
        50
```

<210> SEQ ID NO 6
<211> LENGTH: 51
<212> TYPE: PRT
<213> ORGANISM: Human

<400> SEQUENCE: 6

```
Cys Leu Thr Pro Ala Asp Arg Gly Leu Cys Arg Ala Asn Glu Asn Arg
1               5                   10                  15

Phe Tyr Tyr Asn Ser Val Ile Gly Lys Cys Arg Pro Phe Lys Tyr Ser
            20                  25                  30

Gly Cys Gly Gly Asn Glu Asn Asn Phe Thr Ser Lys Gln Glu Cys Leu
            35                  40                  45

Arg Ala Cys
        50
```

<210> SEQ ID NO 7
<211> LENGTH: 51
<212> TYPE: PRT
<213> ORGANISM: Human

<400> SEQUENCE: 7

-continued

```
Cys Leu Leu Pro Leu Asp Tyr Gly Pro Cys Arg Ala Leu Leu Arg
1               5                   10                  15

Tyr Tyr Tyr Asp Arg Tyr Thr Gln Ser Cys Arg Gln Phe Leu Tyr Gly
            20                  25                  30

Gly Cys Glu Gly Asn Ala Asn Asn Phe Tyr Thr Trp Glu Ala Cys Asp
        35                  40                  45

Asp Ala Cys
    50
```

<210> SEQ ID NO 8
<211> LENGTH: 54
<212> TYPE: PRT
<213> ORGANISM: Human

<400> SEQUENCE: 8

```
Cys Arg Leu Gln Val Ser Val Asp Asp Gln Cys Glu Gly Ser Thr Glu
1               5                   10                  15

Lys Tyr Phe Phe Asn Leu Ser Ser Met Thr Cys Glu Lys Phe Phe Ser
            20                  25                  30

Gly Gly Cys His Arg Asn Arg Ile Glu Asn Arg Phe Pro Asp Glu Ala
        35                  40                  45

Thr Cys Met Gly Phe Cys
    50
```

<210> SEQ ID NO 9
<211> LENGTH: 51
<212> TYPE: PRT
<213> ORGANISM: Human

<400> SEQUENCE: 9

```
Cys Tyr Ser Pro Lys Asp Glu Gly Leu Cys Ser Ala Asn Val Thr Arg
1               5                   10                  15

Tyr Tyr Phe Asn Pro Arg Tyr Arg Thr Cys Asp Ala Phe Thr Tyr Thr
            20                  25                  30

Gly Cys Gly Gly Asn Asp Asn Asn Phe Val Ser Arg Glu Asp Cys Lys
        35                  40                  45

Arg Ala Cys
    50
```

<210> SEQ ID NO 10
<211> LENGTH: 51
<212> TYPE: PRT
<213> ORGANISM: Human

<400> SEQUENCE: 10

```
Cys Leu Val Ser Lys Val Val Gly Arg Cys Arg Ala Ser Met Pro Arg
1               5                   10                  15

Trp Trp Tyr Asn Val Thr Asp Gly Ser Cys Gln Leu Phe Val Tyr Gly
            20                  25                  30

Gly Cys Asp Gly Asn Ser Asn Asn Tyr Leu Thr Lys Glu Glu Cys Leu
        35                  40                  45

Lys Lys Cys
    50
```

<210> SEQ ID NO 11
<211> LENGTH: 51
<212> TYPE: PRT
<213> ORGANISM: Human

-continued

<400> SEQUENCE: 11

Cys Thr Ala Asn Ala Val Thr Gly Pro Cys Arg Ala Ser Phe Pro Arg
1               5                   10                  15

Trp Tyr Phe Asp Val Glu Arg Asn Ser Cys Asn Asn Phe Ile Tyr Gly
            20                  25                  30

Gly Cys Arg Gly Asn Lys Asn Ser Tyr Arg Ser Glu Glu Ala Cys Met
        35                  40                  45

Leu Arg Cys
    50

<210> SEQ ID NO 12
<211> LENGTH: 499
<212> TYPE: DNA
<213> ORGANISM: Human
<220> FEATURE:
<221> NAME/KEY: misc_feature
<222> LOCATION: (160)
<223> OTHER INFORMATION: n is A, T, C, or G
<221> NAME/KEY: misc_feature
<222> LOCATION: (223)
<223> OTHER INFORMATION: n is A, T, C, or G
<221> NAME/KEY: misc_feature
<222> LOCATION: (269)
<223> OTHER INFORMATION: n is A, T, C, or G
<221> NAME/KEY: misc_feature
<222> LOCATION: (279)
<223> OTHER INFORMATION: n is A, T, C, or G
<221> NAME/KEY: misc_feature
<222> LOCATION: (286)
<223> OTHER INFORMATION: n is A, T, C, or G
<221> NAME/KEY: misc_feature
<222> LOCATION: (313)
<223> OTHER INFORMATION: n is A, T, C, or G
<221> NAME/KEY: misc_feature
<222> LOCATION: (331)
<223> OTHER INFORMATION: n is A, T, C, or G
<221> NAME/KEY: misc_feature
<222> LOCATION: (334)
<223> OTHER INFORMATION: n is A, T, C, or G
<221> NAME/KEY: misc_feature
<222> LOCATION: (338)
<223> OTHER INFORMATION: n is A, T, C, or G
<221> NAME/KEY: misc_feature
<222> LOCATION: (340)
<223> OTHER INFORMATION: n is A, T, C, or G
<221> NAME/KEY: misc_feature
<222> LOCATION: (348)
<223> OTHER INFORMATION: n is A, T, C, or G
<221> NAME/KEY: misc_feature
<222> LOCATION: (350)
<223> OTHER INFORMATION: n is A, T, C, or G
<221> NAME/KEY: misc_feature
<222> LOCATION: (385)
<223> OTHER INFORMATION: n is A, T, C, or G
<221> NAME/KEY: misc_feature
<222> LOCATION: (387)
<223> OTHER INFORMATION: n is A, T, C, or G
<221> NAME/KEY: misc_feature
<222> LOCATION: (395)
<223> OTHER INFORMATION: n is A, T, C, or G
<221> NAME/KEY: misc_feature
<222> LOCATION: (417)
<223> OTHER INFORMATION: n is A, T, C, or G
<221> NAME/KEY: misc_feature
<222> LOCATION: (422)
<223> OTHER INFORMATION: n is A, T, C, or G
<221> NAME/KEY: misc_feature
<222> LOCATION: (430)
<223> OTHER INFORMATION: n is A, T, C, or G
<221> NAME/KEY: misc_feature
<222> LOCATION: (432)
<223> OTHER INFORMATION: n is A, T, C, or G
<221> NAME/KEY: misc_feature
<222> LOCATION: (453)

<223> OTHER INFORMATION: n is A, T, C, or G
<221> NAME/KEY: misc_feature
<222> LOCATION: (458)
<223> OTHER INFORMATION: n is A, T, C, or G
<221> NAME/KEY: misc_feature
<222> LOCATION: (465)
<223> OTHER INFORMATION: n is A, T, C, or G
<221> NAME/KEY: misc_feature
<222> LOCATION: (473)
<223> OTHER INFORMATION: n is A, T, C, or G

<400> SEQUENCE: 12

```
cgagggcgcg agtaaggagc agacccaggc atcgcgcgcc gagaaggccg ggcgtcccca      60
cactgaaggt ccggaaaggc gacttccggg ggctttggca cctggcggac cctcccggag     120
cgtcggcacc tgaacgcgag cgcgctccatt gcgcgtgcgn tttgaggggc ttcccgcacc    180
tgatcgcgag accccaacgg ctggtggcgt cgctgcgcgt ctnggctgag ctggccatgg     240
cgcagtgttg cgggcttgag gcggacgcng cgtttntngc ctgctnggat cgctgcttct     300
ctctggggtc ctngcggccg accgagaacg nagnatcnan gattttttncn tggtgtcgaa    360
gttggtggga aattccgggc ttcantncta agtgntgtaa atttaattac ggtcctncaa     420
tntttttttan tngggtttac ggaaagaata atnacttnca agagnttctt aanaatttca    480
ttaaaannat caaggtact                                                  499
```

<210> SEQ ID NO 13
<211> LENGTH: 287
<212> TYPE: DNA
<213> ORGANISM: Human
<220> FEATURE:
<221> NAME/KEY: misc_feature
<222> LOCATION: (182)
<223> OTHER INFORMATION: n is A, C, T, or G
<221> NAME/KEY: misc_feature
<222> LOCATION: (193)
<223> OTHER INFORMATION: n is A, C, T, or G
<221> NAME/KEY: misc_feature
<222> LOCATION: (229)
<223> OTHER INFORMATION: n is A, C, T, or G

<400> SEQUENCE: 13

```
agtcactggg ccttgccgtg catccttccc acgctggtac tttgacgtgg agaggaactc      60
ctgcaataac ttcatctatg gaggctgccg gggcaataag aacagctacc gctctgagga     120
ggcctgcatg ctccgctgct tccgccagca ggagaatcct cccctgcccc ttggctcaaa     180
gntggtggtt ctngcggggc tgttcgtgat ggtgttgatc ctcttcctng gagcctccat     240
ggtctacctt atccgggtgg cacggaggaa ccaggagcgt gccctgc                   287
```

<210> SEQ ID NO 14
<211> LENGTH: 273
<212> TYPE: DNA
<213> ORGANISM: Human
<220> FEATURE:
<221> NAME/KEY: misc_feature
<222> LOCATION: (32)
<223> OTHER INFORMATION: n is A, T, C, or G
<221> NAME/KEY: misc_feature
<222> LOCATION: (58)
<223> OTHER INFORMATION: n is A, T, C, or G
<221> NAME/KEY: misc_feature
<222> LOCATION: (71)
<223> OTHER INFORMATION: n is A, T, C, or G
<221> NAME/KEY: misc_feature
<222> LOCATION: (72)
<223> OTHER INFORMATION: n is A, T, C, or G
<221> NAME/KEY: misc_feature
<222> LOCATION: (73)

```
<223> OTHER INFORMATION: n is A, T, C, or G
<221> NAME/KEY: misc_feature
<222> LOCATION: (95)
<223> OTHER INFORMATION: n is A, T, C, or G
<221> NAME/KEY: misc_feature
<222> LOCATION: (103)
<223> OTHER INFORMATION: n is A, T, C, or G
<221> NAME/KEY: misc_feature
<222> LOCATION: (252)
<223> OTHER INFORMATION: n is A, T, C, or G

<400> SEQUENCE: 14 tttttttat tctaaagggg aaggcccctt tntattaaac ttgtacattt tactttcntt      60
ctttcagaat nnnaataaaa aacttttgtt tatacttaaa aaaaccataa atcagacaaa    120
caaaagaaac gattccaaca tcacttctgt gatgagaaaa gaggcaatgg aattcaacat   180
aagcaaagaa aactntacct ggnggaaaga aatcgatcag cgaggaaaca actcggggct   240
gctgccagac tncaggccat gcgaggagga gcc                                273

<210> SEQ ID NO 15
<211> LENGTH: 256
<212> TYPE: DNA
<213> ORGANISM: Human
<220> FEATURE:
<221> NAME/KEY: misc_feature
<222> LOCATION: (203)
<223> OTHER INFORMATION: n is A, T, C, or G

<400> SEQUENCE: 15 tttttttat tctaaagggg aaggcccctt tttattaaac ttgtacattt tactttcctt      60
ctttcagaat gctaataaaa aacttttgtt tatacttaaa aaaaccataa atcagacaaa    120
caaaagaaac gattccaaca tcacttctgt gatgagaaaa gaggcaatgg aattcaacat   180
aagcaaagaa aactctacct ggnggaaaga aatcgatcag cgaggaaaca actcggggct   240
gctgccagac tgcagg                                                   256

<210> SEQ ID NO 16
<211> LENGTH: 496
<212> TYPE: DNA
<213> ORGANISM: Human
<220> FEATURE:
<221> NAME/KEY: misc_feature
<222> LOCATION: (21)
<223> OTHER INFORMATION: n is A, T, C, or G
<221> NAME/KEY: misc_feature
<222> LOCATION: (27)
<223> OTHER INFORMATION: n is A, T, C, or G
<221> NAME/KEY: misc_feature
<222> LOCATION: (50)
<223> OTHER INFORMATION: n is A, T, C, or G
<221> NAME/KEY: misc_feature
<222> LOCATION: (63)
<223> OTHER INFORMATION: n is A, T, C, or G
<221> NAME/KEY: misc_feature
<222> LOCATION: (142)
<223> OTHER INFORMATION: n is A, T, C, or G
<221> NAME/KEY: misc_feature
<222> LOCATION: (160)
<223> OTHER INFORMATION: n is A, T, C, or G
<221> NAME/KEY: misc_feature
<222> LOCATION: (205)
<223> OTHER INFORMATION: n is A, T, C, or G
<221> NAME/KEY: misc_feature
<222> LOCATION: (207)
<223> OTHER INFORMATION: n is A, T, C, or G
<221> NAME/KEY: misc_feature
<222> LOCATION: (237)
<223> OTHER INFORMATION: n is A, T, C, or G
<221> NAME/KEY: misc_feature
```

```
<222> LOCATION: (254)
<223> OTHER INFORMATION: n is A, T, C, or G
<221> NAME/KEY: misc_feature
<222> LOCATION: (310)
<223> OTHER INFORMATION: n is A, T, C, or G
<221> NAME/KEY: misc_feature
<222> LOCATION: (316)
<223> OTHER INFORMATION: n is A, T, C, or G
<221> NAME/KEY: misc_feature
<222> LOCATION: (333)
<223> OTHER INFORMATION: n is A, T, C, or G
<221> NAME/KEY: misc_feature
<222> LOCATION: (334)
<223> OTHER INFORMATION: n is A, T, C, or G
<221> NAME/KEY: misc_feature
<222> LOCATION: (335)
<223> OTHER INFORMATION: n is A, T, C, or G
<221> NAME/KEY: misc_feature
<222> LOCATION: (342)
<223> OTHER INFORMATION: n is A, T, C, or G
<221> NAME/KEY: misc_feature
<222> LOCATION: (345)
<223> OTHER INFORMATION: n is A, T, C, or G
<221> NAME/KEY: misc_feature
<222> LOCATION: (348)
<223> OTHER INFORMATION: n is A, T, C, or G
<221> NAME/KEY: misc_feature
<222> LOCATION: (351)
<223> OTHER INFORMATION: n is A, T, C, or G
<221> NAME/KEY: misc_feature
<222> LOCATION: (360)
<223> OTHER INFORMATION: n is A, T, C, or G
<221> NAME/KEY: misc_feature
<222> LOCATION: (361)
<223> OTHER INFORMATION: n is A, T, C, or G
<221> NAME/KEY: misc_feature
<222> LOCATION: (370)
<223> OTHER INFORMATION: n is A, T, C, or G
<221> NAME/KEY: misc_feature
<222> LOCATION: (373)
<223> OTHER INFORMATION: n is A, T, C, or G
<221> NAME/KEY: misc_feature
<222> LOCATION: (377)
<223> OTHER INFORMATION: n is A, T, C, or G
<221> NAME/KEY: misc_feature
<222> LOCATION: (379)
<223> OTHER INFORMATION: n is A, T, C, or G
<221> NAME/KEY: misc_feature
<222> LOCATION: (384)
<223> OTHER INFORMATION: n is A, T, C, or G
<221> NAME/KEY: misc_feature
<222> LOCATION: (389)
<223> OTHER INFORMATION: n is A, T, C, or G
<221> NAME/KEY: misc_feature
<222> LOCATION: (396)
<223> OTHER INFORMATION: n is A, T, C, or G
<221> NAME/KEY: misc_feature
<222> LOCATION: (399)
<223> OTHER INFORMATION: n is A, T, C, or G
<221> NAME/KEY: misc_feature
<222> LOCATION: (402)
<223> OTHER INFORMATION: n is A, T, C, or G
<221> NAME/KEY: misc_feature
<222> LOCATION: (403)
<223> OTHER INFORMATION: n is A, T, C, or G
<221> NAME/KEY: misc_feature
<222> LOCATION: (406)
<223> OTHER INFORMATION: n is A, T, C, or G
<221> NAME/KEY: misc_feature
<222> LOCATION: (408)
<223> OTHER INFORMATION: n is A, T, C, or G
<221> NAME/KEY: misc_feature
<222> LOCATION: (411)
<223> OTHER INFORMATION: n is A, T, C, or G
<221> NAME/KEY: misc_feature
<222> LOCATION: (414)
<223> OTHER INFORMATION: n is A, T, C, or G
<221> NAME/KEY: misc_feature
<222> LOCATION: (415)
```

<223> OTHER INFORMATION: n is A, T, C, or G
<221> NAME/KEY: misc_feature
<222> LOCATION: (416)
<223> OTHER INFORMATION: n is A, T, C, or G
<221> NAME/KEY: misc_feature
<222> LOCATION: (428)
<223> OTHER INFORMATION: n is A, T, C, or G
<221> NAME/KEY: misc_feature
<222> LOCATION: (429)
<223> OTHER INFORMATION: n is A, T, C, or G
<221> NAME/KEY: misc_feature
<222> LOCATION: (431)
<223> OTHER INFORMATION: n is A, T, C, or G
<221> NAME/KEY: misc_feature
<222> LOCATION: (436)
<223> OTHER INFORMATION: n is A, T, C, or G
<221> NAME/KEY: misc_feature
<222> LOCATION: (439)
<223> OTHER INFORMATION: n is A, T, C, or G
<221> NAME/KEY: misc_feature
<222> LOCATION: (441)
<223> OTHER INFORMATION: n is A, T, C, or G
<221> NAME/KEY: misc_feature
<222> LOCATION: (444)
<223> OTHER INFORMATION: n is A, T, C, or G
<221> NAME/KEY: misc_feature
<222> LOCATION: (445)
<223> OTHER INFORMATION: n is A, T, C, or G
<221> NAME/KEY: misc_feature
<222> LOCATION: (447)
<223> OTHER INFORMATION: n is A, T, C, or G
<221> NAME/KEY: misc_feature
<222> LOCATION: (450)
<223> OTHER INFORMATION: n is A, T, C, or G
<221> NAME/KEY: misc_feature
<222> LOCATION: (452)
<223> OTHER INFORMATION: n is A, T, C, or G
<221> NAME/KEY: misc_feature
<222> LOCATION: (457)
<223> OTHER INFORMATION: n is A, T, C, or G
<221> NAME/KEY: misc_feature
<222> LOCATION: (467)
<223> OTHER INFORMATION: n is A, T, C, or G
<221> NAME/KEY: misc_feature
<222> LOCATION: (473)
<223> OTHER INFORMATION: n is A, T, C, or G
<221> NAME/KEY: misc_feature
<222> LOCATION: (492)
<223> OTHER INFORMATION: n is A, T, C, or G

<400> SEQUENCE: 16

| | | | | | |
|---|---|---|---|---|---|
| aattcggcac | gaggtacaat | ntcactnacg | gatcctgcca | gctgtttgtn | tatgggggct | 60 |
| gtnacggaaa | cagcaataat | tacctgacca | aggaggagtg | cctcaagaaa | tgtgccactg | 120 |
| tcacagagaa | tgccacgggt | gncctggcca | ccagcaggan | tgcagcggat | tcctctgtcc | 180 |
| caagtgctcc | cagaaggcag | gattntnaag | accactccag | cggtatgttc | aactatngag | 240 |
| gatacttgca | ccgncaacgg | agttcactag | ggctttgccg | tgcatccttt | tcccacggtt | 300 |
| ggtactttn | aacggnggag | gaggaacttc | ctnnnaataa | anttnatntt | ntgggnggtn | 360 |
| ntccggggn | atnaagnanc | aatnaccgnt | tttaanggng | gnnttnantt | ntcnnntttt | 420 |
| tttccccnna | ngggnttnt | nccnntnccn | tnggtanaaa | gggggntt | ttngggatt | 480 |
| ttttggaaaa | tnaaat | | | | | 496 |

<210> SEQ ID NO 17
<211> LENGTH: 201
<212> TYPE: DNA
<213> ORGANISM: Human
<220> FEATURE:
<221> NAME/KEY: misc_feature
<222> LOCATION: (22)
<223> OTHER INFORMATION: n is A, T, C, or G
<221> NAME/KEY: misc_feature
<222> LOCATION: (108)
<223> OTHER INFORMATION: n is A, T, C, or G

<400> SEQUENCE: 17
gaggaaccag gagcgtgccc tncgcaccgt ctggagctcc ggagatgaca aggagcagct    60
ggtgaagaac acatatgtcc tgtgaccgcc ctgtcgccaa gaggactngg gaagggaggg   120
gagactatgt gtgagctttt tttaaataga gggattgact cggatttgag tgatcattag   180
ggctgaggtc tgtttctctg g                                             201

<210> SEQ ID NO 18
<211> LENGTH: 419
<212> TYPE: DNA
<213> ORGANISM: Human
<220> FEATURE:
<221> NAME/KEY: misc_feature
<222> LOCATION: (57)
<223> OTHER INFORMATION: n is A, T, C, or G
<221> NAME/KEY: misc_feature
<222> LOCATION: (63)
<223> OTHER INFORMATION: n is A, T, C, or G
<221> NAME/KEY: misc_feature
<222> LOCATION: (110)
<223> OTHER INFORMATION: n is A, T, C, or G
<221> NAME/KEY: misc_feature
<222> LOCATION: (116)
<223> OTHER INFORMATION: n is A, T, C, or G
<221> NAME/KEY: misc_feature
<222> LOCATION: (118)
<223> OTHER INFORMATION: n is A, T, C, or G
<221> NAME/KEY: misc_feature
<222> LOCATION: (144)
<223> OTHER INFORMATION: n is A, T, C, or G
<221> NAME/KEY: misc_feature
<222> LOCATION: (174)
<223> OTHER INFORMATION: n is A, T, C, or G
<221> NAME/KEY: misc_feature
<222> LOCATION: (183)
<223> OTHER INFORMATION: n is A, T, C, or G
<221> NAME/KEY: misc_feature
<222> LOCATION: (185)
<223> OTHER INFORMATION: n is A, T, C, or G
<221> NAME/KEY: misc_feature
<222> LOCATION: (252)
<223> OTHER INFORMATION: n is A, T, C, or G
<221> NAME/KEY: misc_feature
<222> LOCATION: (319)
<223> OTHER INFORMATION: n is A, T, C, or G
<221> NAME/KEY: misc_feature
<222> LOCATION: (352)
<223> OTHER INFORMATION: n is A, T, C, or G
<221> NAME/KEY: misc_feature
<222> LOCATION: (357)
<223> OTHER INFORMATION: n is A, T, C, or G
<221> NAME/KEY: misc_feature
<222> LOCATION: (361)
<223> OTHER INFORMATION: n is A, T, C, or G
<221> NAME/KEY: misc_feature
<222> LOCATION: (369)
<223> OTHER INFORMATION: n is A, T, C, or G
<221> NAME/KEY: misc_feature
<222> LOCATION: (372)
<223> OTHER INFORMATION: n is A, T, C, or G
<221> NAME/KEY: misc_feature
<222> LOCATION: (397)
<223> OTHER INFORMATION: n is A, T, C, or G
<221> NAME/KEY: misc_feature
<222> LOCATION: (416)
<223> OTHER INFORMATION: n is A, T, C, or G

<400> SEQUENCE: 18
ggcagaggtc ttcccgcacc taaatcgcaa gaccccaacg gctggtggcg tcgctgnccc    60

```
gtntcggctg ggctggccat ggcgcatgtg ccgggcctga ggcggaccgn cgtttntngc      120
ctgctgggaa tcgctgctcc tttntgtggt cctggcggcc gaccgaaaac gccngcatcc      180
acnanttctg cctggtgtcg aaggtggtgg gcagatgccg ggcctccatg cctaggtggt      240
ggtacaatgt tnactaacgg atcctggcca gttttgtgt atgggggct tttaacggga        300 aacagcaata atttaactng accaaggagg agttgccttc aagaaatgtt gnccatnttt      360
naaaagggna tncccagggg ttaacctggg ccaccanagg gatttaaggg gttttnttt       419
```

```
<210> SEQ ID NO 19
<211> LENGTH: 437
<212> TYPE: DNA
<213> ORGANISM: Human
<220> FEATURE:
<221> NAME/KEY: misc_feature
<222> LOCATION: (26)
<223> OTHER INFORMATION: n is A, T, C, or G
<221> NAME/KEY: misc_feature
<222> LOCATION: (83)
<223> OTHER INFORMATION: n is A, T, C, or G
<221> NAME/KEY: misc_feature
<222> LOCATION: (227)
<223> OTHER INFORMATION: n is A, T, C, or G
<221> NAME/KEY: misc_feature
<222> LOCATION: (258)
<223> OTHER INFORMATION: n is A, T, C, or G
<221> NAME/KEY: misc_feature
<222> LOCATION: (278)
<223> OTHER INFORMATION: n is A, T, C, or G
<221> NAME/KEY: misc_feature
<222> LOCATION: (288)
<223> OTHER INFORMATION: n is A, T, C, or G
<221> NAME/KEY: misc_feature
<222> LOCATION: (306)
<223> OTHER INFORMATION: n is A, T, C, or G
<221> NAME/KEY: misc_feature
<222> LOCATION: (313)
<223> OTHER INFORMATION: n is A, T, C, or G
<221> NAME/KEY: misc_feature
<222> LOCATION: (355)
<223> OTHER INFORMATION: n is A, T, C, or G
<221> NAME/KEY: misc_feature
<222> LOCATION: (356)
<223> OTHER INFORMATION: n is A, T, C, or G
<221> NAME/KEY: misc_feature
<222> LOCATION: (360)
<223> OTHER INFORMATION: n is A, T, C, or G
<221> NAME/KEY: misc_feature
<222> LOCATION: (397)
<223> OTHER INFORMATION: n is A, T, C, or G
<221> NAME/KEY: misc_feature
<222> LOCATION: (398)
<223> OTHER INFORMATION: n is A, T, C, or G
<221> NAME/KEY: misc_feature
<222> LOCATION: (404)
<223> OTHER INFORMATION: n is A, T, C, or G
<221> NAME/KEY: misc_feature
<222> LOCATION: (408)
<223> OTHER INFORMATION: n is A, T, C, or G
<221> NAME/KEY: misc_feature
<222> LOCATION: (410)
<223> OTHER INFORMATION: n is A, T, C, or G
<221> NAME/KEY: misc_feature
<222> LOCATION: (434)
<223> OTHER INFORMATION: n is A, T, C, or G

<400> SEQUENCE: 19
```

```
gaattcggca gagcccgtga cttccnccag caggagaatc ctcccctgcc ccttggctca      60
aaggccctgg aagcccacct ccnagaagcc cggtgtgggg gcgggccacg ggggagaatc     120
ccaagctcag tccccacaaa gttcaggccc ggtcggaggc aggggcaggt ccgggtccaa     180
agcaaggaca ccacagctct tccgaactcc agcagcagct tccagcnatt tcggaacacg     240
```

```
gatgtaaagt tcccacgnct tgctggcttc caagcacnac ggagaagnca ttccccgggg      300
caaggnccaa agnaaggccc caaaagttga aggaagaagg gaggaagggg caagnnaggn      360
ggaaggggca agaaggaagg aggtttcccc catttgnnag gggncttngn acaggtttcc      420
atttaaaacc tttnctt                                                    437
```

<210> SEQ ID NO 20
<211> LENGTH: 31
<212> TYPE: DNA
<213> ORGANISM: synthetic construct

<400> SEQUENCE: 20

```
cgcagatctc gcagcatcca cgacttctgc c                                     31
```

<210> SEQ ID NO 21
<211> LENGTH: 34
<212> TYPE: DNA
<213> ORGANISM: synthetic construct

<400> SEQUENCE: 21

```
cgcaagcttt taggcattct ctgtgacagt ggca                                  34
```

<210> SEQ ID NO 22
<211> LENGTH: 37
<212> TYPE: DNA
<213> ORGANISM: synthetic construct

<400> SEQUENCE: 22

```
ccccggatcc agcgatatgt tcaactatga agaatac                               37
```

<210> SEQ ID NO 23
<211> LENGTH: 34
<212> TYPE: DNA
<213> ORGANISM: synthetic construct

<400> SEQUENCE: 23

```
ccccaagctt ttaattctcc tgctggcgga agca                                  34
```

<210> SEQ ID NO 24
<211> LENGTH: 35
<212> TYPE: DNA
<213> ORGANISM: synthetic construct

<400> SEQUENCE: 24

```
ccccagatct cgaacgcagc atccacgact tctgc                                 35
```

<210> SEQ ID NO 25
<211> LENGTH: 36
<212> TYPE: DNA
<213> ORGANISM: synthetic construct

<400> SEQUENCE: 25

```
cccctctaga ttaattctcc tgctggcgga agcagc                                36
```

<210> SEQ ID NO 26
<211> LENGTH: 38
<212> TYPE: DNA
<213> ORGANISM: synthetic construct

<400> SEQUENCE: 26

```
ccccagatct gccatcatgg cgcagctgtg cgggctga                              38
```

```
<210> SEQ ID NO 27
<211> LENGTH: 30
<212> TYPE: DNA
<213> ORGANISM: synthetic construct

<400> SEQUENCE: 27
cgctctagat cacaggacat atgtgttctt                                          30

<210> SEQ ID NO 28
<211> LENGTH: 51
<212> TYPE: PRT
<213> ORGANISM: synthetic construct
<220> FEATURE:
<221> NAME/KEY: misc_feature
<222> LOCATION: (22)
<223> OTHER INFORMATION: Xaa is any amino acid
<221> NAME/KEY: misc_feature
<222> LOCATION: (28)
<223> OTHER INFORMATION: Xaa is any amino acid

<400> SEQUENCE: 28

Cys Leu Leu Pro Ala Asp Thr Gly Pro Cys Arg Ala Ser Ile Thr Arg
1               5                   10                  15

Tyr Phe Tyr Asn Val Xaa Thr Gly Ser Cys Glu Xaa Phe Val Tyr Gly
            20                  25                  30

Gly Cys Gly Gly Asn Arg Asn Asn Phe Glu Ser Leu Glu Glu Cys Lys
        35                  40                  45

Arg Ala Cys
    50

<210> SEQ ID NO 29
<211> LENGTH: 15
<212> TYPE: PRT
<213> ORGANISM: Human
<220> FEATURE:
<221> NAME/KEY: misc_feature
<222> LOCATION: (11)
<223> OTHER INFORMATION: Xaa is any amino acid

<400> SEQUENCE: 29

Ala Asp Arg Glu Arg Ser Ile His Asp Phe Xaa Leu Val Ser Lys
1               5                   10                  15

<210> SEQ ID NO 30
<211> LENGTH: 29
<212> TYPE: PRT
<213> ORGANISM: Human
<220> FEATURE:
<221> NAME/KEY: misc_feature
<222> LOCATION: (6)
<223> OTHER INFORMATION: Xaa is any amino acid
<221> NAME/KEY: misc_feature
<222> LOCATION: (22)
<223> OTHER INFORMATION: Xaa is any amino acid

<400> SEQUENCE: 30

Lys Val Val Gly Arg Xaa Arg Ala Ser Met Pro Arg Trp Trp Tyr Asn
1               5                   10                  15

Val Thr Asp Gly Ser Xaa Gln Leu Phe Val Tyr Gly Gly
            20                  25

<210> SEQ ID NO 31
<211> LENGTH: 26
<212> TYPE: PRT
<213> ORGANISM: Human
```

-continued

```
<400> SEQUENCE: 31

Ala Thr Val Thr Glu Asn Ala Thr Gly Asp Leu Ala Thr Ser Arg Asn
1               5                   10                  15

Ala Ala Asp Ser Ser Val Pro Ser Ala Pro
                20                  25
```

METHODS OF MEASURING TISSUE FACTOR PATHWAY INHIBITOR-3

CROSS-REFERENCE TO RELATED APPLICATIONS

This application is a divisional of U.S. application Ser. No. 09/013,896, filed Jan. 27, 1998, now U.S. Pat. No. 6,262,233, which claims benefit of U.S. Provisional Application No. 60/036,703, filed Jan. 31, 1997; each of which are incorporated herein by reference in its entirety.

STATEMENT REGARDING FEDERALLY-SPONSORED RESEARCH AND DEVELOPMENT

Not applicable.

REFERENCE TO MICROFICHE APPENDIX/ SEQUENCE LISTING/TABLE/COMPUTER PROGRAM LISTING APPENDIX (submitted on a compact disc and an incorporation-by-reference of the material on the compact disc) Not applicable.

BACKGROUND OF THE INVENTION

1. Field of the Invention

The present invention relates to a novel human gene encoding a polypeptide which is a member of the Kunitz-type protease inhibitor family. More specifically. isolated nucleic acid molecules are provided encoding a human polypeptide named Tissue Factor Pathway Inhibitor-3 hereinafter referred to TFPI-3. TFPI-3 polypeptides are also provided, as are vectors, host cells and recombinant methods for producing the same. Also provided are diagnostic methods for detecting disorders related to vascular hemostatsis and therapeutic methods for treating such disorders. The invention further relates to screening methods for identifying agonists and antagonists of TFPI-3.

2. Background Art

Proteases are responsible, either directly or indirectly, for all bodily functions, including cell growth, differentiation and death (apoptosis), cell nutrition, intra- and extracellular protein turnover (housekeeping and repair), cell migration and invasion. and fertilization and implantation. These functions extend from the cellular level to the organ and organism level to produce cascade systems such as hemostatis and inflamation, and complex processes at all levels of physiology and pathophysiology.

Maintenance of vascular integrity is an important host response to injury. Complex hemostatis mechanisms of coagulation, platelet function, and fibrinolysis exist to minimize adverse consequences of vascular injury and to accelerate vascular repair. Many of these hemostatic mechanisms are initiated and/or regulated by cells of the wall of the blood vessel.

Tissue-factor-pathway inhibitor (TFPI) is a cell-surface associated glycoprotein which plays a key role in the regulation of tissue factor-initiated blood coagulation. Human TFPI is a trace 42-kDa plasma glycoprotein that is synthesized primarily by endothelial cells and consists of a negatively charged amino terminal region, three tandem Kunitz-type inhibitor domains, and a highly basic carboxyl-terminal tail (Wun, T. C., et al., J. Biol. Chem. 263:6001 (1988)). After a 22-residue signal peptide, the mature protein contains 213 amino acids with 18 cysteines. TFPI forms a complex with factor Xa and inhibits its amidolytic and proteolytic activity. The factor Xa-TFPI complex rapidly inhibits activity of the factor VIIa-tissue factor complex.

The cloning and characterization of a gene coding for a second tissue factor pathway inhibitor (TFPI-2), has been reported (Sprecher, C. A. et al., Proc. Natl. Acad, Sci. USA, 91, 3353–3357 (1994)). This gene was initially identified on the basis of primary sequence homology and structural similarity. Subsequent characterization has confirmed its predicted activity as a protease inhibitor. Alterations of the hemostatic system can result from such causes as neoplasia and trauma. Such alterations result in an increased incidence of thrombotic disorders such as venous thrombosis. pulmonary embolism, atrial fibrillation, cerebral thrombosis, and hemophilia. Thus, there is a need for identification and characterization of polypeptides that function as inhibitors of the coagulation pathway which can play a role in detecting, preventing, ameliorating or correcting such disorders.

SUMMARY OF THE INVENTION

The present invention provides isolated nucleic acid molecules comprising a polynucleotide encoding at least a portion of the TFPI-3 polypeptide having the complete amino acid sequence shown in SEQ ID NO:2 or the complete amino acid sequence encoded by the cDNA clone deposited as plasmid DNA as ATCC Deposit Number 97797 on Nov. 20, 1996. The nucleotide sequence determined by sequencing the deposited TFPI-3 clone, which is shown in FIGS, 1A and 1B (SEQ ID NO:1), contains an open reading frame encoding a complete polypeptide of 252 amino acid residues, including an initiation codon encoding an N-terminal methionine at nucleotide positions 361 to 363 and a predicted molecular weight of about 28.2 kDa.

The TFPI-3 protein of the present invention shares sequence homology with the translation product of the human mRNA for Tissue Factor Pathway Inhibitor (TFPI), TFPI-2 and aprotinin, including the following conserved domains: (a) a first predicted Kunitz-type domain of about 51 amino acids; and (b) a second predicted Kunitz-type domain also of about 51 amino acids, both of which are thought to be important in regulating blood coagulation, and are underscored with stars in FIGS. 1A and 1B. The homology between human TFPI, TFPI-2, aprotinin and TFPI-3, shown in FIG. 2, indicates that TFPI-3 is also a protease and may be involved in regulating blood coagulation. Protease inhibition assays described herein confirm the ability of TFPI-3 polypeptides to inhibit protease activity.

The encoded polypeptide has a predicted leader sequence of 27 amino acids underlined in FIGS. 1A and 1B; and the amino acid sequence of the predicted mature TFPI-3 protein is also shown in FIGS. 1A and 1B, and as amino acid residues 1–225 (SEQ ID NO:2).

Thus, one aspect of the invention provides an isolated nucleic acid molecule comprising a polynucleotide having a nucleotide sequence selected from the group consisting of: (a) a nucleotide sequence encoding a polypeptide comprising the predicted second Kunitz-type domain of the TFPI-3 polypeptide having the amino acid sequence at positions 106 to 156 in SEQ ID NO:2 or as encoded by the cDNA clone contained in ATCC Deposit No. 97797; (b) a nucleotide sequence encoding a polypeptide comprising the consensus Kunitz-type domain having the amino acid sequence shown as SEQ ID NO:28; and (c) a nucleotide sequence complementary to any of the nucleotide sequences in (a) or (b) above; wherein said nucleic acid sequence in (a) or (b) does not encode a polypeptide comprising a sequence shown as SEQ ID NO:29, SEQ ID NO:30, or SEQ ID NO:31.

Further embodiments of the invention include isolated nucleic acid molecules that comprise a polynucleotide having a nucleotide sequence at least 90% identical. and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TFPI-3 polypeptide having an amino acid sequence in (a) or (b), above.

The present invention also relates to recombinant vectors, which include the isolated nucleic acid molecules of the present invention, and to host cells containing the recombinant vectors, as well as to methods of making such vectors and host cells and for using them for production of TFPI-3 polypeptides or peptides by recombinant techniques.

The invention further provides an isolated TFPI-3 polypeptide comprising an amino acid sequence selected from the group consisting of: (a) the amino acid sequence of the polypeptide comprising the predicted second Kunitz-type domain of the TFPI-3 polypeptide having the amino acid sequence at positions 106 to 156 in SEQ ID NO:2 or as encoded by the cDNA clone contained in ATCC Deposit No. 97797; or (b) the amino acid sequence of the polypeptide comprising the consensus Kunitz-type domain having the amino acid sequence of SEQ ID NO:28; wherein said nucleic acid sequence in (a) or (b) does not encode a polypeptide comprising a sequence shown as SEQ ID NO:29, SEQ ID NO:30, or SEQ ID NO:31.

The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a TFPI-3 polypeptide having an amino acid sequence described in (a) or (b), above. Peptides or polypeptides having the amino acid sequence of an epitope-bearing portion of a TFPI-3 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a TFPI-3 polypeptide having an amino acid sequence described in (a) or (b) above. The invention further provides methods for isolating antibodies that bind specifically to a TFPI-3 polypeptide having an amino acid sequence as described herein. Such antibodies are useful diagnostically or therapeutically as described below.

The invention also provides for pharmaceutical compositions comprising TFPI-3 polypeptides, particularly human TFPI-3 polypeptides, which may be employed, for instance, in inhibiting intravascular clotting and preventing the formation of fribrin clots both in vitro and in vivo, for anticoagulant therapy in prophylaxis of venous thrombosis and as treatment for preventing its extension, as well as to provide low-dose regiment for prevention of postoperative deep venous thrombosis and pulmonary embolism, for the prophlaxis and treatment of pulmonary embolism and atrial fibrillation with embolism, to prevent clotting in arterial and heart surgery as well as for prevention of cerebral thrombosis in evolving stroke, for treating coronary occlusion with acute myocardial infarction and in the prophylaxis and treatment of peripheral arterial emoblism, for the treatment of sepsis, inflamatory diseases and transplant rejection, in the treatment of hyperfibrinolytic hemorrhage and traumatic hemorrhagic shock as well as in diseases connected with excessive release of pancreatic elastase (pancreatitis), serum elastase (artherosclerosis), leukocyte elastase in acute and chronic inflammation with damage to connective tissue, in damage to vessel walls, in necrotic diseases, and in degeneration of lung tissue. Methods of treating individuals in need of TFPI-3 polypeptides are also provided.

The invention further provides compositions comprising a TFPI-3 polynucleotide or a TFPI-3 polypeptide for administration to cells in vitro, to cells ex vivo and to cells in vivo, or to a multicellular organism. In certain particularly preferred embodiments of this aspect of the invention, the compositions comprise a TFPI-3 polynucleotide for expression of a TFPI-3 polypeptide in a host organism for treatment of disease. Particularly preferred in this regard is expression in a human patient for treatment of a dysfunction associated with aberrant endogenous activity of a TFPI-3.

The present invention also provides a screening method for identifying compounds capable of enhancing or inhibiting a biological activity of the TFPI-3 polypeptide, which involves contacting a protease which is inhibited by TFPI-3 polypeptide with the candidate compound in the presence of a TFPI-3 polypeptide and a substrate cleavable by the selected protease, assaying the inhibitory activity of the protease activity of the protease in the presence of the candidate compound and of TFPI-3 polypeptide, and comparing the protease activity to a standard level of activity, the standard being assayed when contact is made between the protease and substrate in the presence of the TFPI-3 polypeptide, and in the absence of the candidate compound. In this assay, an increase in inhibitory activity over the standard indicates that the candidate compound is an agonist of TFPI-3 activity and a decrease in inhibitory activity compared to the standard indicates that the compound is an antagonist of TFPI-3 activity.

It has been discovered that TFPI-3 is expressed at differing levels in some tissues. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the hemostatic system, significantly higher or lower levels of TFPI-3 gene expression may be detected in certain tissues (e.g., cancerous and wounded tissues) or bodily fluids (e.g., serum, plasma, urine, synovial fluid or spinal fluid) taken from an individual having such a disorder, relative to a "standard" TFPI-3 gene expression level, i.e., the TFPI-3 expression level in healthy tissue from an individual not having the hemostatic system disorder. Thus, the invention provides a diagnostic method useful during diagnosis of such a disorder, which involves: (a) assaying TFPI-3 gene expression level in cells or body fluid of an individual; (b) comparing the TFPI-3 gene expression level with a standard TFPI-3 gene expression level, whereby an increase or decrease in the assayed TFPI-3 gene expression level compared to the standard expression level is indicative of disorder in the hemostatic.

An additional aspect of the invention is related to a method for treating an individual in need of an increased level of TFPI-3 activity in the body comprising administering to such an individual a composition comprising a therapeutically effective amount of an isolated TFPI-3 polypeptide of the invention or an agonist thereof.

A still further aspect of the invention is related to a method for treating an individual in need of a decreased level of TFPI-3 activity in the body comprising, administering to such an individual a composition comprising a therapeutically effective amount of an TFPI-3 antagonist. Preferred antagonists for use in the present invention are TFPI-3-specific antibodies and TFPI-3 proteins having an amino acid residue other than arginine at the P1 residue of either the first or second Kunitz-type domain, positions 21 and 116 of SEQ ID NO:2, respectively.

BRIEF DESCRIPTION OF THE FIGURES

FIG. 1 shows the nucleotide sequence (SEQ ID NO:1) and deduced amino acid sequence (SEQ ID NO:2) of TFPI-3. The predicted leader sequence of about 27 amino acids is underlined. The leader sequence has positions −27 to −1 in SEQ ID NO:2. The first Kunitz-type domain (Kunitz-1) has positions 11–61 in SEQ ID NO:2 and the second Kunitz-type domain (Kunitz-2) has positions 106 to 156 in SEQ ID NO:2, both of which are underscored with stars in FIGS. 1A and 1B.

FIG. 2 shows the regions of identity between the amino acid sequences of the Kunitz-type domains of TFPI-3 (Kunitz-1 SEQ ID NO:10, Kunitz-2 SEQ ID NO:11), the Kunitz-type domains of TFPI-1 (Kunitz-1 SEQ ID NO:4, Kunitz-2 SEQ ID NO:5, Kunitz-3 SEQ ID NO:6), the Kunitz-type domains of TFPI-2 (Kunitz-1 SEQ ID NO:7, Kunitz-2 SEQ ID NO:8, Kunitz-3 SEQ ID NO:9) and aprotinin (SEQ ID NO:3), as determined by the Clustal method using the computer program "Megalign" contained in the DNAStar suite of programs. This program generates a consensus sequence; i.e., a consensus Kunitz-type domain, which is shown as SEQ ID NO:28.

DETAILED DESCRIPTION

Figure 3:
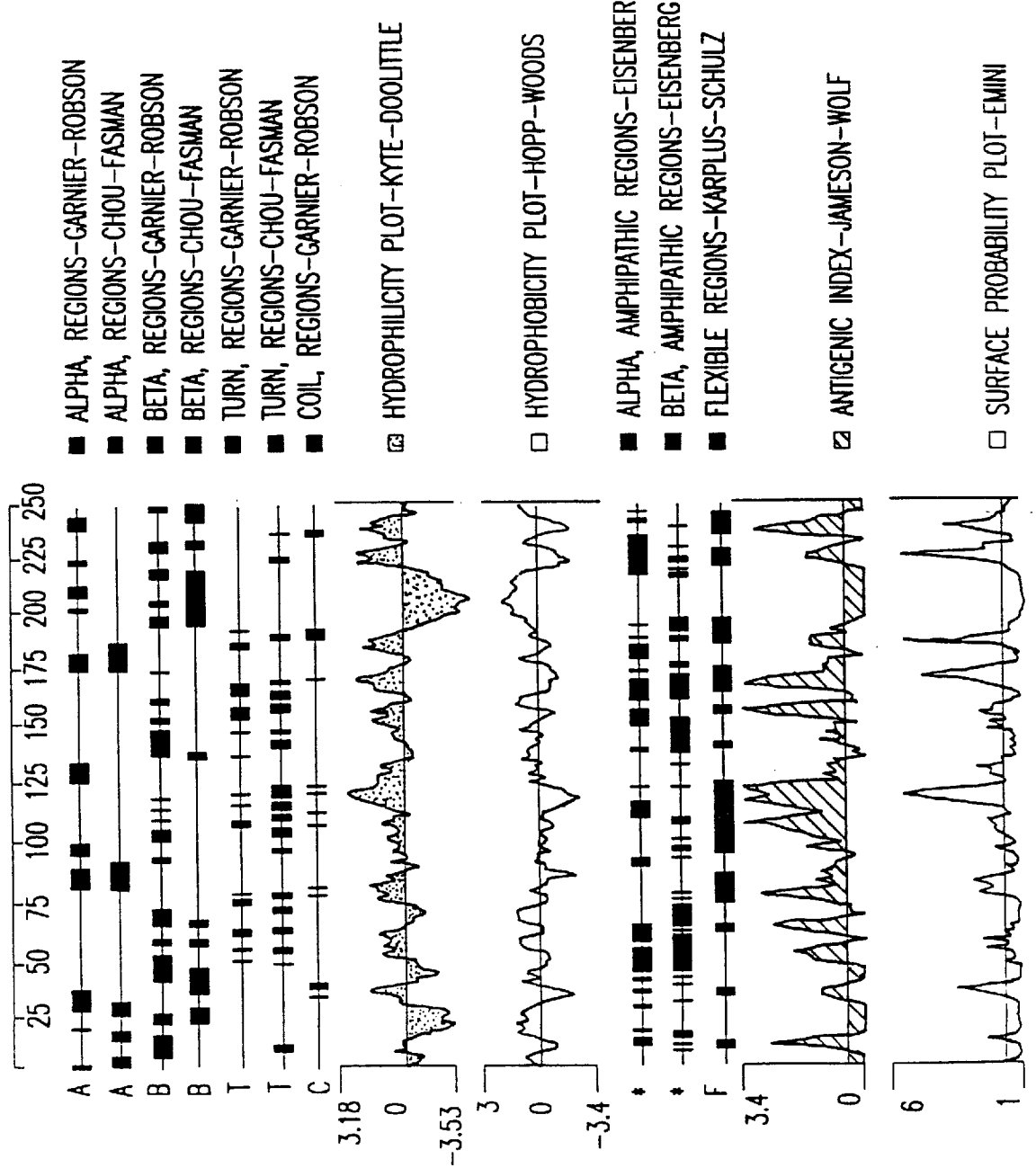
FIG. 3 shows an analysis of the TFPI-3 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the TFPI-3 protein, i.e., regions from which epitope-bearing peptides of the invention can be obtained.

The present invention provides isolated nucleic acid molecules comprising a polynucleotide encoding a Tissue Factor Pathway Inhibitor-3 ("TFPI-3") polypeptide having the amino acid sequence shown in SEQ ID NO:2, which was determined by sequencing a cloned cDNA. The nucleotide sequence shown in FIGS. 1A and 1B (SEQ ID NO:1) was obtained by sequencing the HOEBN05 clone, which was deposited on Nov. 20, 1996 at the American Type Culture Collection, 110801 University Boulevard, Manassas, Va. 20110-2209. The deposited clone is contained in the pBluescript SK(−) plasmid (Stratagene, La Jolla. Calif.).

The TFPI-3 protein of the present invention shares sequence homology with the translation product of the human mRNAs for TFPI, TFPI-2 and aprotinin. More specifically, the TFPI-3 contains two Kunitz type protease inhibitor domains which share striking similarity to the Kunitz-type domains from proteases TFPI, TFPI-2 and aprotinin as can be seen in FIG. 2, including nearly perfect conservation among all six cysteines contained in each. TFPI and TFPI-2 are thought to be important protease inhibitors acting to mediate hemostatis through an interaction with Factor Xa and inhibition of the Factor VIIa-tissue factor complex in the blood coagulation cascade. Aprotinin likewise is an important protease inhibitor which has become a valuable drug, named Tyrasylol-®, for treatment of various diseases like, e.g., hyperfibrinolytic hemmorrhage and traumatic-hemorrhagic shock (Fritz, H. et al., Drug Res., 33:479–494 (1983), and see, for example, U.S. Pat. No. 4,894,439).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and 1B (SEQ ID NO:1), a nucleic acid molecule of the present invention encoding a TFPI-3 polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from osteoblasts. Additional clones of the same gene were also identified in cDNA libraries from the following tissues: human fetal brain, fetal kidney, placenta, pituitary, testis, testis tumor, pancreas tumor, and macrophage.

The determined nucleotide sequence of the TFPI-3 cDNA of FIGS. 1A and 1B (SEQ ID NO:1) contains an open reading frame encoding a protein of 252 amino acid residues, with an initiation codon at nucleotide positions 361 to 363 of the nucleotide sequence in FIGS. 1A and 1B (SEQ ID NO:1), and a deduced molecular weight of about 28.2 kDa. The amino acid sequence of the TFPI-3 protein shown in SEQ ID NO:2 is about 24% identical to human mRNA for TFPI-2 (Sprecher, C. A. et al., PNAS USA, 91:3353 (1994), which can be accessed on GenBank as Accession No. L27624).

As mentioned above, the open reading frame of the TFPI-3 gene shares sequence homology with the translation product of the human mRNAs for TFPI, TFPI-2 and aprotinin (FIG. 2), including the following conserved domains: (a) a first Kunitz-type domain of about 51 amino acids; and (b) a second Kunitz-type domain also of about 51 amino acids. The homology between TFPI, TFPI-2, aprotinin and TFPI-3 indicates that TFPI-3 may also be a protease inhibitor. Experiments described in Example 5 with a recombinantly cloned first Kunitz-type domain of TFPI-3 (construction shown in Example 1), have shown that TFPI-3 polypeptides have the ability to inhibit protease activity. Taken together this data indicates that TFPI-3 has protease inhibiting activity and may be important in regulation of blood coagulation.

As one of ordinary skill would appreciate, due to the possibilities of sequencing errors discussed above, the actual complete TFPI-3 polypeptide encoded by the deposited cDNA, which comprises about 252 amino acids, may be somewhat longer or shorter. More generally, the actual open reading frame may be anywhere in the range of ±20 amino acids, more likely in the range of ±10 amino acids, of that predicted from the first methionine codon from the N-terminus shown in FIGS. 1A and 1B (SEQ ID NO:1). It will further be appreciated that, depending on the analytical criteria used for identifying various functional domains, the exact "address" of the Kunitz-type domains of the TFPI-3 polypeptide may differ slightly from the predicted positions above. For example, the exact location of the TFPI-3 Kunitz-type domains in SEQ ID NO:2 may vary slightly (e.g., the address may "shift" by about 1 to about 10 residues, more likely about 1 to about 5 residues) depending on the criteria used to define the domain. In this case, the ends of the Kunitz-type domains were predicted on the basis of similarity between the TFPI-3 amino acid sequence and the sequence of several other mammalian proteases, and in particular on the basis of the six conserved cysteines contained within each domain.

Leader and Mature Sequences

The amino acid sequence of the complete TFPI-3 protein includes a leader sequence and a mature protein, as shown in SEQ ID NO:2. More in particular, the present invention provides nucleic acid molecules encoding a mature form of the TFPI-3 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TFPI-3 polypeptide having the amino acid sequence encoded by the cDNA clone contained in the host identified as ATCC Deposit No. 97797. By the "mature TFPI-3 polypeptide having the amino acid sequence encoded by the cDNA clone in ATCC Deposit No. 97797" is meant the mature form(s) of the TFPI-3 protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (Virus Res. 3:271–286 (1985)) uses the information from a short N-terminal charged region and a subsequent uncharged region of the complete (uncleaved) protein. The method of von Heinje (Nucleic Acids Res. 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete TFPI-3 polypeptide was analyzed by a computer program "PSORT", available from Dr. Kenta Nakai of the Institute for Chemical Research, Kyoto University (see K. Nakai and M. Kanehisa, Genomics 14:897–911 (1992)), which is an expert system for predicting the cellular location of a protein based on the amino acid sequence. As part of this computational prediction of localization, the methods of McGeoch and von Heinje are incorporated. The analysis of the TFPI-3 amino acid sequence by this program predicted one cleavage site within the complete amino acid sequence shown in SEQ ID NO:2.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 361 to 363 of the nucleotide sequence shown in FIGS. 1A and 1B (SEQ ID NO:1).

Also included are DNA molecules comprising the coding sequence for the predicted mature TFPI-3 protein shown at positions 442–1116 of SEQ ID NO:2.

In addition, isolated nucleic acid molecules of the invention include DNA molecules which comprise a sequence substantially different from those described above but which, due to the degeneracy of the genetic code, still encode the TFPI-3 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the TFPI-3 polypeptide having an amino acid sequence encoded by the cDNA clone contained in the plasmid deposited as ATCC Deposit No. 97797 on Nov. 20, 1996. Preferably, this nucleic acid molecule will encode the mature polypeptide, or a soluble extracellular form of the polypeptide containing one or both Kunitz-type domains (but lacking the transmembrane portion, about amino acids 196 to 225 in SEQ ID NO:2), encoded by the above-described deposited cDNA clone.

The invention further provides an isolated nucleic acid molecule having the nucleotide sequence shown in FIGS. 1A and 1B (SEQ ID NO:1) or the nucleotide sequence of the TFPI-3 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the TFPI-3 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 442–1116 of SEQ ID NO:1.

In addition, the invention provides nucleic acid molecules having nucleotide sequences related to extensive portions of SEQ ID NO:1 which have been determined from the following related cDNA clones: HFCBP02R (SEQ ID NO:12), HKDH23F (SEQ ID NO:13), HPLBH53R (SEQ ID NO:14), HPLBH50R (SEQ ID NO:15), HCOSD62R (SEQ ID NO:16), HEPAB48R (SEQ ID NO:17), HAUAR79R (SEQ ID NO:18), and HPTTL69R (SEQ ID NO: 19).

Polypeptides related to SEQ ID NO:2 include: Ala Asp Arg Glu Arg Ser Ile His Asp Phe Xaa Leu Val Ser Lys (SEQ ID NO:29); Lys Val Val Gly Arg Xaa Arg Ala Ser Met Pro Arg Trp Trp Tyr Asn Val Thr Asp Gly Ser Xaa Gin Leu Phe Val Tyr Gly Gly (SEQ ID NO:30); and Ala Thr Val Thr Glu Asn Ala Thr Gly Asp Leu Ala Thr Ser Arg Asn Ala Ala Asp Ser Ser Val Pro Ser Ala Pro (SEQ ID NO:31).

Further, the invention includes a polynucleotide comprising any portion of at least about 30 nucleotides, preferably at least about 50 nucleotides, of SEQ ID NO:1 from nucleotide 361 to 1116. The invention preferably includes a polynucleotide comprising any portion of at least about 30 nucleotides, preferably at least about 50 nucleotides, of SEQ ID NO:1 from nucleotide 442 to 910. The invention most preferably includes a polynucleotide comprising any portion of at least about 30 nucleotides, preferably at least about 50 nucleotides, of SEQ ID NO:1 from nucleotide 442 to 631.

More generally, by a fragment of an isolated nucleic acid molecule having the nucleotide sequence of the deposited cDNA or the nucleotide sequence shown in FIGS. 1A and 1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A and 1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and 1B (SEQ ID NO:1). Preferred nucleic acid fragments of the present invention include nucleic acid molecules encoding epitope-bearing portions of the TFPI-3 polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97797. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5x Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and 1B (SEQ ID NO:1)). Of course, a polynucleotide which hybridizes only to a poly A sequence (such as the 3' terminal poly(A) tract of the TFPI-3 cDNA shown in FIGS. 1A and 1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a TFPI-3 polypeptide may include, but are not limited to those encoding the amino acid sequence of the mature polypeptide, by itself; and the coding sequence for the mature polypeptide and additional sequences, such as those encoding the about 27 amino acid leader or secretory sequence, such as a pre-, or pro- or prepro- protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the TFPI-3 fused to Fc at the N- or C-terminus.

Variant and Mutant Polynucleotides

The present invention further relates to variants of the nucleic acid molecules of the present invention, which encode portions, analogs or derivatives of the TFPI-3 protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TFPI-3 protein or portions thereof. Also especially preferred in this regard are conservative substitutions.

Most highly preferred are nucleic acid molecules encoding the mature protein having the amino acid sequence shown in SEQ ID NO:2 or the mature TFPI-3 amino acid sequence encoded by the deposited cDNA clone.

Thus, one aspect of the invention provides an isolated nucleic acid molecule comprising a polynucleotide having a nucleotide sequence selected from the group consisting of: (a) a nucleotide sequence encoding a polypeptide comprising the predicted second Kunitz-type domain of the TFPI-3 polypeptide having the amino acid sequence at positions 106 to 156 in SEQ ID NO:2 or as encoded by the cDNA clone contained in ATCC Deposit No. 97797; (b) a nucleotide sequence encoding a polypeptide comprising the consensus Kunitz-type domain having the amino acid sequence shown in SEQ ID NO:28; and (c) a nucleotide sequence complementary to any of the nucleotide sequences in (a) or (b), above; except that said polynucleotide of (a) or (b) does not encode a polypeptide comprising a sequence shown as SEQ ID NO:29, SEQ ID NO:30, or SEQ ID NO:31.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TFPI-3 polypeptide having an amino acid sequence in (a) or (b), above.

The present invention also relates to recombinant vectors, which include the isolated nucleic acid molecules of the present invention, and to host cells containing the recombinant vectors, as well as to methods of making such vectors and host cells and for using them for production of TFPI-3 polypeptides or peptides by recombinant techniques.

By a polynucleotide having a nucleotide sequence at least, for example, 95% "identical" to a reference nucleotide sequence encoding a TFPI-3 polypeptide is intended that the nucleotide sequence of the polynucleotide is identical to the reference sequence except that the polynucleotide sequence may include up to five point mutations per each 100 nucleotides of the reference nucleotide sequence encoding the TFPI-3 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A and 1B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIGS. 1A and 1B (SEQ ID NO:1) or to the nucleic acid sequence of the deposited cDNA, irrespective of whether they encode a polypeptide having TFPI-3 activity. This is because even where a particular nucleic acid molecule does not encode a polypeptide having TFPI-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TFPI-3 activity include, inter alia, (1) isolating the TFPI-3 gene or allelic variants thereof in a cDNA library; (2) in situ hybridization (e.g., "FISH") to metaphase chromosomal spreads to provide precise chromosomal location of the TFPI-3 gene, as described in Verma et al., Human Chromosomes: A Manual of Basic Techniques, Pergamon Press, New York (1988); and Northern Blot analysis for detecting TFPI-3 mRNA expression in specific tissues.

Preferred, however, are nucleic acid molecules having sequences at least 90%, 95%, 96%, 97%, 98% or 99% identical to the nucleic acid sequence shown in FIGS. 1A and 1B (SEQ ID NO:1) or to the nucleic acid sequence of the deposited cDNA which do, in fact, encode a polypeptide having TFPI-3 protein activity. By "a polypeptide having TFPI-3 activity" is intended polypeptides exhibiting activity similar, but not necessarily identical, to an activity of the mature TFPI-3 protein of the invention, as measured in a particular biological assay. For example, the TFPI-3 protein of the present invention inhibits the protease activity of trypsin and the amidolytic activity of factor VIIa-tissue factor. An in vitro assay for measuring the trypsin inhibitory activity of TFPI-3 is described in the literature, for example, in Sprecher, C. A. et al., Proc. Natl. Acad, Sci. USA, 91, 3353–3357 (1994). Briefly, the assay involves coincubating TFPI-3 with trypsin and subsequently measuring residual protease activity by measuring the activity of a chromogenic substrate. Such activity is useful for preventing the coagulation of blood. Other such assays are known to those of skill in the art, for example, as disclosed on page 13 in U.S. Pat. No. 4,894,436, incorporated herein by reference.

TFPI-3 protein modulates protease activity in a dose-dependent manner in the above-described assay. Thus, "a polypeptide having TFPI-3 protein activity" includes polypeptides that also exhibit any of the same protease inhibitory activities in the above-described assays in a dose-dependent manner. Although the degree of dose-dependent activity need not be identical to that of the TFPI-3 protein, preferably, "a polypeptide having TFPI-3 protein activity" will exhibit substantially similar dose-dependence in a given activity as compared to the TFPI-3 protein (i.e., the candidate polypeptide will exhibit greater activity or not more than about 25-fold less and, preferably, not more than about tenfold less activity relative to the reference TFPI-3 protein). TFPI-3 polypeptides may also be assayed for activity according to the assay described in Example 5, below.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A and 1B (SEQ ID NO:1) will encode a polypeptide "having TFPI-3 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TFPI-3 protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of TFPI-3 polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al, *J. Biol. Chem.* 270:9459–9471 (1995).

The TFPI-3 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated TFPI-3 polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of TFPI-3 polypeptides, protein engineering maybe employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified, in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Holst et al., Thrombosis and Haemostasis, 71(2):214–19 (1994) reported a modified TFPI protein that retained antithrombotic activity despite containing only the first 161 amino acids of a 276 amino acid protein. In the present case, since the protein of the invention is a member of the TFPI polypeptide family, deletions of N-terminal amino acids up to the cysteine at position 106 (C106) of SEQ ID NO:2 may retain some biological activity such as protease inhibitor activity. Polypeptides having further N-terminal deletions including the C106 residue in SEQ ID NO:2 would not be expected to retain biological activity of the second Kunitz-type domain because it is known that this residue in a TFPI-related polypeptide is required for forming a disulfide bridge in the second Kunitz-type domain which provides the conformation necessary for interaction with its protease substrate.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or Kunitz-type domain containing form of the protein generally will be retained when less than the majority of the residues of the complete or Kunitz-type domain containing form of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the TFPI-3 shown in SEQ ID NO:2, up to the cysteine residue at position number 106, and polynucleotides encoding such polypeptides. In particular, the present invention provides polypeptides comprising the amino acid sequence of residues n-225 of SEQ ID NO:2, where n is an integer in the range of 99 to 106. C106 is the position of the first residue from the N-terminus of the complete TFPI-3 polypeptide (shown in SEQ ID NO:2) believed to be required for protease inhibitory activity of the second Kuntiz-type domain of the complete TFPI-3 protein.

More in particular, the invention provides polynucleotides encoding polypeptides having the amino acid sequence of residues of 99 to 225, 100 to 225, 101 to 225, 102 to 225, 103 to 225, 104 to 225, 105 to 225 and 106 to 225 of SEQ ID NO:2. Polynucleotides encoding these polypeptides also are provided.

Similarly, many examples of biologically functional C-terminal deletion muteins are known. In the present case, since the protein of the invention is a member of the TFPI polypeptide family, deletions of C-terminal amino acids up to the cysteine at position 156 (C156) of SEQ ID NO:2 may retain some biological activity such as antithromotic/ protease inhibitor activity. Polypeptides having further C-terminal deletions including C156 of SEQ ID NO:2 would not be expected to retain such biological activities because it is known that this residue in a TFPI-related polypeptide is required for forming a disulfide bridge in the second Kunitz-type domain which provides the conformation necessary for interaction with (and inhibition of proteolytic and amidolytic activity of) factor Xa.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or Kunitz-type domain containing form of the protein generally will be retained when less than the majority of the residues of the complete or Kunitz-type domain containing form of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of TFPI-3 shown in SEQ ID NO:2, up to the C156 of SEQ ID NO:2, and polynucleotides encoding such polypeptides. In particular, the present invention provides polypeptides having the amino acid sequence of residues 99 to m of the amino acid sequence in SEQ ID NO:2, where m is any integer in the range of 156–225, and residue C156 is the position of the first residue from the C-terminus of the complete TFPI-3 polypeptide (shown in SEQ ID NO:2) believed to be required for amidolytic and proteolytic inhibitory activity of the second Kunitz-type domain of the complete TFPI-3 protein.

More in particular, the invention provides polynucleotides encoding polypeptides having the amino acid sequence of residues 99 to 156, 99 to 157, 99 to 158, 99 to 159, 99 to 160, 99 to 161, 99 to 162, 99 to 163, 99 to 164, 99 to 165, 99 to 166, 99 to 167, 99 to 168, 99 to 160, 99 to 170, 99 to 171, 99 to 172, 99 to 173, 99 to 174, 99 to 175, 99 to 176, 99 to 177, 99 to 178, 99 to 179, 99 to 180, 99 to 181, 99 to 182, 99 to 183, 99 to 184, 99 to 185, 99 to 186, 99 to 187, 99 to 188, 99 to 189, 99to 190, 99 to 191, 99 to 192, 99 to 193, 99 to 194, 99 to 195, 99to 196, 99 to 197, 99 to 198, 99 to 199, 99 to 200, 99 to 201, 99 to 202, 99 to 203, 99 to 204, 99 to 205, 99 to 206, 99 to 207, 99 to 208, 99 to 209, 99 to 210, 99 to 211, 99 to 212, 99 to 213, 99 to 214, 99 to 215, 99 to 216, 99 to 217, 99 to 218, 99 to 219, 99 to 220, 99 to 221, 99 to 222, 99 to 223, 99 to 224, and 99 to 225 of SEQ ID NO:2. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above.

Also included are a nucleotide sequence encoding a polypeptide consisting of a portion of the complete TFPI-3 amino acid sequence encoded by the cDNA clone contained in ATCC Deposit No. 97797, where this portion excludes from 126 to about 132 amino acids from the amino terminus of the complete amino acid sequence encoded by the cDNA clone contained in ATCC Deposit No. 97797; or from 1 to about 69 amino acids from the carboxy terminus, or any combination of the above amino terminal and carboxy terminal deletions, of the complete amino acid sequence encoded by the cDNA clone contained in ATCC Deposit No. 97797. Polynucleotides encoding all of the above deletion mutant polypeptide forms also are provided.

Other Mutants

In addition to terminal deletion forms of the protein discussed above, it also will be recognized by one of ordinary skill in the art that some amino acid sequences of the TFPI-3 polypeptide can be varied without significant effect of the structure or function of the protein. If such differences in sequence are contemplated, it should be remembered that there will be critical areas on the protein which determine activity.

Thus, the invention further includes variations of the TFPI-3 polypeptide which show substantial TFPI-3 polypeptide activity or which include regions of TFPI-3 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which a Kunitz-type domain containing polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the TFPI-3 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TFPI-3 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vivo or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

FIG. 2 shows an alignment of nine Kunitz-type domains. Preferred are TFPI-3 polypeptides having strongly conserved amino acids as shown in the Kunitz consensus sequence SEQ ID NO:28. Where a TFPI-3 polypeptide has an amino acid residue which is not identical to an amino acid at the same position in the consensus sequence, the amino acid in the TFPI-3 polypeptide mutein is preferably replaced with the amino acid shown in the consensus sequence. Most highly preferred TFPI-3 muteins are those having the amino acid sequence shown as the consensus sequence (SEQ ID NO:28). Polynucleotides encoding such polypeptides are also provided. Such polypeptides can easily be produced by method known to those of skill in the are, for example, by solid phases synthesis methods.

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Since TFPI-3 is a member of the TFPI-related protein family, to modulate rather than completely eliminate biological activities of TFPI-3 preferably mutations are made in sequences encoding amino acids in the TFPI-3 conserved Kunitz-type domains, i.e., in positions 11–61 and 106–156 of SEQ ID NO:2, more preferably in residues within this region which are not conserved in similar Kunitz-type domains among other protease inhibitors (see FIG. 3). More in particular, factor VIIa-tissue factor exhibits a kinetic preference for synthetic substrates with a P1 arginine residue (Kam, Ch.M. et al., *Thromb. Haemostas.*, 64:133–137 (1990)). Accordingly, replacement of the arginine at position 21 or position 116 of SEQ ID NO:2 with another amino acid results in a TFPI-3 mutant with conformational integrity but decreased activity; i.e., antagonists. Thus, forming part of the invention are polypeptides comprising an amino acid sequence of the full-length TFPI-3, the mature TFPI-3 or a Kunitz-type domain containing form of TFPI-3 wherein the amino acid at position 21 and/or 116 of SEQ ID NO:2 is other than arginine. Also forming part of the present invention are isolated polynucleotides comprising nucleic acid sequences which encode the above TFPI-3 mutants.

The polypeptides of the present invention are preferably provided in an isolated form, and preferably are substantially purified. A recombinantly produced version of the TFPI-3 polypeptide can be substantially purified by the one-step method described in Smith and Johnson, *Gene* 67:31–40 (1988). Polypeptides of the invention also can be purified from natural or recombinant sources using anti-TFPI-3 antibodies of the invention in methods which are well known in the art of protein purification.

The invention further provides an isolated TFPI-3 polypeptide comprising an amino acid sequence selected from the group consisting of: (a) the amino acid sequence of a consensus Kunitz-domain having the amino acid sequence shown as SEQ ID NO:28; and (b) the amino acid sequence of a polypeptide comprising the second Kunitz-type domain of TFPI-3 having the amino acid sequence at positions 106 to 156 in SEQ ID NO:2, or as encoded by the cDNA clone contained in ATCC Deposit NO. 97797; wherein the polypeptide of (a) or (b) does not comprise a sequence shown as SEQ ID NO:29, SEQ ID NO:30, or SEQ ID NO:31.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a TFPI-3 polypeptide is intended that the amino acid sequence of the polypeptide is identical to the reference sequence except that the polypeptide sequence may include up to five amino acid alterations per each 100 amino acids of the reference amino acid of the TFPI-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 5371 1). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below. the polypeptides of the present invention can also be used to raise polyclonal and monoclonal antibodies, which are useful in assays for detecting TFPI-3 protein expression as described below or as agonists and antagonists capable of enhancing or inhibiting TFPI-3 protein function. Further, such polypeptides can be used in the yeast two-hybrid system to "capture" TFPI-3 protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," Science, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al.; Cell 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate TFPI-3-specific antibodies include: a polypeptide comprising amino acid residues from about Asn-47 to about Cys-61 in SEQ ID NO:2; a polypeptide comprising amino acid residues from about Asp-71 to about Thr-107; a polypeptide comprising amino acid residues from about Glu-127 to about Asn-133; and a polypeptide comprising amino acid residues from about Asn-142 to about Glu-150. These polypeptide fragments have been determined to bear antigenic epitopes of the TFPI-3 protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." Proc. Natl. Acad. Sci. USA 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Immunogenic epitope-bearing peptides of the invention, i.e., those parts of a protein that elicit an antibody response when the whole protein is the immunogen. are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al., (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, TFPI-3 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric TFPI-3 protein or protein fragment alone (Fountoulakis et al., *J. Biochem.* 270:3958–3964 (1995)).

Antibodies

TFPI-3-protein specific antibodies for use in the present invention can be raised against the intact TFPI-3 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to TFPI-3 protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the TFPI-3 protein or an antigenic fragment thereof can be administered to an animal in order to induce the production of sera containing polyclonal antibodies. In a preferred method, a preparation of TFPI-3 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TFPI-3 protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a TFPI-3 protein antigen or, more preferably, with a TFPI-3 protein-expressing cell. Suitable cells can be recognized by their capacity to bind anti-TFPI-3 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the TFPI-3 protein antigen.

Alternatively, additional antibodies capable of binding to the TFPI-3 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, TFPI-3-protein specific antibodies are used to immunize an animal, preferably a mouse. The splenocytes of such an animal are then used to produce hybridoma cells, and the hybridoma cells are screened to identify clones which produce an antibody whose ability to bind to the TFPI-3 protein-specific antibody can be blocked by the TFPI-3 protein antigen. Such antibodies comprise anti-idiotypic antibodies to the TFPI-3 protein-specific antibody and can be used to immunize an animal to induce formation of further TFPI-3 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, TFPI-3 protein-binding fragments can be produced through the application of recombinant DNA technology or through synthetic chemistry.

For in vivo use of anti-TFPI-3 in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Hemostatic System-Related Disorders

Diagnosis

For a number of hemostatic system-related disorders, substantially altered (increased or decreased) levels of TFPI-3 gene expression can be detected in endothelial tissue or other cells or bodily fluids (e.g., sera, plasma, urine, synovial fluid or spinal fluid) taken from an individual having such a disorder, relative to a "standard" TFPI-3 gene expression level, that is, the TFPI-3 expression level in endothelial tissue or bodily fluids from an individual not having the hemostatic system disorder. Thus, the invention provides a diagnostic method useful during diagnosis of a hemostatic disorder, which involves measuring the expression level of the gene encoding the TFPI-3 protein in endothelial tissue or other cells or body fluid from an individual and comparing the measured gene expression level with a standard TFPI-3 gene expression level, whereby an increase or decrease in the gene expression level compared to the standard is indicative of an hemostatic system disorder.

Thus, the invention provides a diagnostic method useful during diagnosis of a hemostatic system disorder, which involves measuring the expression level of the gene encoding the TFPI-3 protein in endothelial tissue or other cells or body fluid from an individual and comparing the measured gene expression level with a standard TFPI-3 gene expression level, whereby an increase or decrease in the gene expression level compared to the standard is indicative of a hemostatic system disorder.

Where a diagnosis of a disorder in the hemostatic system has already been made according to conventional methods, the present invention is useful as a prognostic indicator, whereby patients exhibiting either enhanced or depressed TFPI-3 gene expression will experience a worse clinical outcome relative to patients expressing the gene at a level nearer the standard level.

By "assaying the expression level of the gene encoding the TFPI-3 protein" is intended qualitatively or quantitatively measuring or estimating the level of the TFPI-3 protein or the level of the mRNA encoding the TFPI-3 protein in a first biological sample either directly (e.g., by determining or estimating absolute protein level or mRNA level) or relatively (e.g., by comparing to the TFPI-3 protein level or mRNA level in a second biological sample). Preferably, the TFPI-3 protein level or mRNA level in the first biological sample is measured or estimated and compared to a standard TFPI-3 protein level or mRNA level, the standard being taken from a second biological sample obtained from an individual not having the disorder or being determined by averaging levels from a population of individuals not having a disorder of the hemostatic system. As will be appreciated in the art, once a standard TFPI-3 protein level or mRNA level is known, it can be used repeatedly as a standard for comparison.

By "biological sample" is intended any biological sample obtained from an individual, body fluid, cell line, tissue culture, or other source which contains TFPI-3 protein or mRNA. As indicated, biological samples include body fluids (such as sera, plasma, urine, synovial fluid and spinal fluid) which contain free TFPI-3 protein, endothelial tissue, and other tissue sources found to express complete or mature (! or "extracellular domain" of the TFPI-3 or a TFPI-3 receptor. Methods for obtaining tissue biopsies and body fluids from mammals are well known in the art. Where the biological sample is to include mRNA, a tissue biopsy is the preferred source.

The present invention is useful for diagnosis or treatment of various hemostatic system-related disorders in mammals, preferably humans. Such disorders include predisposition to vascular thrombosis, particularly in post-stroke and post-cardiac surgery patients, hyperfibrinolytic hemorrhage, traumatic-hemorrhagic shock, and hemophilia, and the like.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the TFPI-3 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying TFPI-3 protein levels in a biological sample can occur using antibody-based techniques. For example, TFPI-3 protein expression in tissues can be studied with classical immunohistological methods (Jalkanen, M., et al., *J. Cell. Biol.* 101.976–985 (1985); Jalkanen, M., et al., *J. Cell. Biol.* 105:3087–3096 (1987)). Other antibody-based methods useful for detecting TFPI-3 protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying TFPI-3 protein levels in a biological sample obtained from an individual, TFPI-3 protein can also be detected in vivo by imaging. Antibody labels or markers for in vivo imaging of TFPI-3 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TFPI-3 protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain TFPI-3 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, TFPI-3 polynucleotides and polypeptides are useful for diagnosis of conditions involving abnormally high or low expression of TFPI-3 activities. Given the activities modulated by TFPI-3, it is readily apparent that a substantially altered (increased or decreased) level of expression of TFPI-3 in an individual compared to the standard or "normal" level produces pathological conditions related to the bodily system(s) in which TFPI-3 is expressed and/or is active.

It will also be appreciated by one of ordinary skill that, since the TFPI-3 protein of the invention is a member of the TFPI-family the mature form of the protein may be released in soluble form(s) from the cells which express TFPI-3 by proteolytic cleavage. Therefore, when soluble TFPI-3 is added from an exogenous source to cells, tissues or the body of an individual, the protein will exert its physiological activities on its target cells of that individual.

Therefore. it will be appreciated that conditions caused by a decrease in the standard or normal level of TFPI-3 activity in an individual, particularly disorders of the hemostasis system, can be treated by administration of mature or Kunitz-type domain containing form of TFPI-3 polypeptide (in a soluble form). Thus, the invention also provides a method of treatment of an individual in need of an increased level of TFPI-3 activity comprising administering to such an individual a pharmaceutical composition comprising an amount of an isolated TFPI-3 polypeptide of the invention, effective to increase the TFPI-3 activity level in such an individual.

Alterations of the hemostatic system resulting in an increased incidence of thrombotic disorders is a frequent consequence of neoplasia. Studies in animal models with TFPI have demonstrated that TFPI infusion abrogates the disseminated intravascular coagulation triggered by TF and prevents arterial reocclusion following thrombolysis of clots induced by vessel injury. Intravascular coagulation is also known to be caused by endotoxin (Bronze, Jr., G.J., Seminars in Hematology, 29(3):159 (1992).

Therefore, TFPI-3 is useful in inhibiting intravascular clotting and preventing the formation of fribrin clots both in vitro and in vivo. The polypeptides of the present invention are particularly useful for anticoagulant therapy in prophylaxis of venous thrombosis and as treatment for preventing its extension, as well as to provide low-dose regiment for prevention of postoperative deep venous thrombosis and pulmonary embolism in patients undergoing major abodominothoracic surgery, particularly those who are at risk of developing thromboembolic disease. TFPI-3 can also be used for the prophlaxis and treatment of pulmonary embolism and atrial fibrillation with embolism. For example, pulmonary embolism represents the leading non-obstetric cause of post-partum death. Thus, TFPI-3 may be used to treat pregnant and post-partum women. Additionally, TFPI-3 can be used to prevent clotting in arterial and heart surgery as well as for prevention of cerebral thrombosis in evolving stroke. TFPI-3 can be used both in treating coronary occlusion with acute myocardial infarction and in the prophylaxis and treatment of peripheral arterial emoblism. TFPI-3 may also be used in to treat sepsis, inflamatory diseases and transplant rejection. TFPI-3 can also be employed as an anticoagulant in blood transfusions, extra-corporeal circulation, and dialysis procedures and in blood samples for laboratory purposes.

Similar to aprotinin, TFPI-3 polypeptides, particularly those containing only one Kunitz-type domain including consensus Kunitz-type domain polypeptides, may be particularly useful in the treatment of hyperfilbronolytic hemorrhage and traumatic hemorrhagic shock as well as in diseases connected with excessive release of pancreatic elastase (pancreatitis), serum elastase (artherosclerosis), leukocyte elastase in acute and chronic inflammation with damage to connective tissue in damage to vessel walls, in necrotic diseases, and degeneration of lung tissue.

Formulations

The TFPI-3 polypeptide composition will be formulated and dosed in a fashion consistent with good medical practice, taking into account the clinical condition of the individual patient (especially the side effects of treatment with TFPI-3 polypeptide alone), the site of delivery of the TFPI-3 polypeptide composition, the method of administration, the scheduling of administration, and other factors known to practitioners. The "effective amount" of TFPI-3 polypeptide for purposes herein is thus determined by such considerations.

As a general proposition, the total pharmaceutically effective amount of TFPI-3 polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TFPI-3 polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the TFPI-3 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The TFPI-3 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release TFPI-3 polypeptide compositions also include liposomally entrapped TFPI-3 polypeptide. Liposomes containing TFPI-3 polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TFPI-3 polypeptide therapy.

For parenteral administration. in one embodiment, the TFPI-3 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example. the formulation preferably does not include oxidizing agents and other compounds that are known to be deleterious to polypeptides.

Generally, the formulations are prepared by contacting the TFPI-3 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TFPI-3 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of TFPI-3 polypeptide salts.

TFPI-3 polypeptide to be used for therapeutic administration must be sterile. Sterility is readily accomplished by filtration through sterile filtration membranes (e.g., 0.2 micron membranes). Therapeutic TFPI-3 polypeptide compositions generally are placed into a container having a sterile access port, for example, an intravenous solution bag or vial having a stopper pierceable by a hypodermic injection needle.

TFPI-3 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TFPI-3 polypeptide solution, and the resulting mixture is lyophilized. The infusion solution is prepared by reconstituting the lyophilized TFPI-3 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of TFPI-3 on cells, such as its interaction with TFPI-3-binding molecules such as receptor molecules. An agonist is a compound which increases the natural biological functions of TFPI-3 or which functions in a manner similar to TFPI-3, while antagonists decrease or eliminate such functions.

In another aspect of this embodiment the invention provides a method for identifying a receptor protein or other ligand-binding protein which binds specifically to a TFPI-3 polypeptide. For example, a cellular compartment, such as a membrane or a preparation thereof, may be prepared from a cell that expresses a molecule that binds TFPI-3. The preparation is incubated with labeled TFPI-3 TFPI-3 and complexes of TFPI-3 bound to the receptor or other binding protein are isolated and characterized according to routine methods known in the art. Alternatively, the TFPI-3 polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds TFPI-3, such as a molecule of a signaling or regulatory pathway modulated by TFPI-3. The preparation is incubated with labeled TFPI-3 in the absence or the presence of a candidate molecule which may be a TFPI-3 agonist or antagonist. The ability of the candidate molecule to bind the binding molecule is reflected in decreased binding of the labeled ligand. Molecules which bind gratuitously, i.e., without inducing the effects of TFPI-3 on binding the TFPI-3 binding molecule, are most likely to be good antagonists. Molecules that bind well and elicit effects that are the same as or closely related to TFPI-3 are agonists.

TFPI-3-like effects of potential agonists and antagonists may by measured, for instance, by determining activity of a second messenger system following interaction of the candidate molecule with a cell or appropriate cell preparation, and comparing the effect with that of TFPI-3 or molecules that elicit the same effects as TFPI-3. Second messenger systems that may be useful in this regard include but are not limited to AMP guanylate cyclase, ion channel or phosphoinositide hydrolysis second messenger systems.

Another example of an assay for TFPI-3 antagonists is a competitive assay that combines TFPI-3 and a potential antagonist with a TFPI-3 substrate under appropriate conditions for a competitive inhibition assay. The substrate can be measured such that the activity of TFPI-3 can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing TFPI-3-induced activities, thereby preventing the action of TFPI-3 by excluding TFPI-3 from binding.

Other potential antagonists include antisense molecules. Antisense technology can be used to control gene expression through antisense DNA or RNA or through triple-helix formation. Antisense techniques are discussed, for example, in Okano, *J. Nieurochem.* 56: 560 (1991 ); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TFPI-3. The antisense RNA oligonucleotide hybridizes to the mRNA in vivo and blocks translation of the mRNA molecule into TFPI-3 polypeptide. The oligonucleotides described above can also be delivered to cells such that the antisense RNA or DNA may be expressed in vivo to inhibit production of TFPI-3 protein.

The agonists and antagonists may be employed in a composition with a pharmaceutically acceptable carrier, e.g., as described above.

The antagonists may be employed for instance to promote coagulation in the treatment of hemophilia. Antibodies against TFPI-3 may be employed to bind to and inhibit TFPI-3 activity to treat hemophilia. Likewise, particularly preferred antagonists are TFPI-3 polypeptides containing only a single Kunitz-type domain wherein the residue at the P1 position is other than Arginine, as described above. Such polypeptides should bind to the same substrate as TFPI-3 but have reduced inhibitory activity. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a TFPI-3 protein gene. This can be accomplished using a variety of well known techniques and libraries, which generally are available commercially. The genomic DNA then is used for in situ chromosome mapping using well known techniques for this purpose.

In addition, in some cases. sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found. for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention. the same will be more readily understood by reference to the following examples, which are provided by way of illustration and are not intended as limiting.

EXAMPLES

Example 1(a)

Expression and Purification of "His-tagged" TFPI Kunitz-type Domains-1 and -2 in *E. coli*

The bacterial expression vector pQE9 (pD10) is used for bacterial expression in this example. (QIAGEN, Inc., 9259 Eton Avenue, Chatsworth, Calif. 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the TFPI-3 protein comprising the first Kunitz-type domains of the TFPI-3 amino acid sequence was amplified from the deposited cDNA clone using PCR oligonucleotide primers which anneal to the 5' sequences of the desired portion of the TFPI-3 cDNA and to sequences in the deposited construct 3' to the cDNA coding sequence. Additional nucleotides containing restriction sites to facilitate cloning in the pQE9 vector were added to the 5' and 3' primer sequences, respectively.

For cloning the first Kunitz-type domain of the TFPI-3 protein, the 5' primer had the sequence 5' CGC AGATCTCGCAGCATCCACGACTTCTGCC 3' (SEQ ID NO:20) containing the underlined BglII restriction site. The 3' primer had the sequence 5' CGC AAGCTTTAGGCATTCTCTGTGACAGTGGCA 3' (SEQ ID NO:21) containing the underlined HindIII restriction site For cloning the second Kunitz-type domain of the TFPI-3 protein, the 5' primer had the sequence 5' CCCC GGATCCAGCGATATGTTCAACTATGAAGAATAC 3' (SEQ ID NO:22) containing the underlined BamHI restriction site. The 3' primer had the sequence 5' CCCC AAGCTTTTAATTCTCCTGCTGGCGGAAGCA 3' (SEQ ID NO:23) containing the underlined HindIII restriction site.

One of ordinary skill in the art would appreciate, of course, that the point in the protein coding sequence where the primer anneals may be varied to amplify a DNA segment encoding any desired portion of the complete TFPI-3 protein shorter or longer than the form of the protein described here.

The amplified TFPI-3 DNA fragment and the vector pQE9 were digested with the appropriate enzymes whose recognition sequence had been built into the primers and the digested DNAs were then ligated together. Insertion of the TFPI-3 DNA into the restricted pQE9 vector places the TFPI-3 protein coding region downstream from the IPTG-inducible promoter and in-frame with an initiating AUG and the six histidine codons.

The ligation mixture was transformed into competent *E. coil* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), was used in carrying out the example described herein. This strain, which is only one of many that are suitable for expressing TFPI-3 protein, is available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with both ampicillin (100 μg/ml) and kanamycin (25 μg/ml). The O/N culture was used to inoculate a large culture, at a dilution of approximately 1:25 to 1:250. The cells were grown to an optical density at 600 nm ("OD600") of between 0.4 and 0.6. Isopropyl-β-D-thiogalactopyranoside ("IPTG") was then added to a final concentration of 1 mM to induce transcription from the lac repressor sensitive promoter, by inactivating the lad repressor. Cells subsequently were incubated further for 3 to 4 hours. Cells then were harvested by centrifugation.

The cells were then stirred for 3–4 hours at 4° C. in 6M guanidine-HCl, pH 8. The cell debris was removed by centrifugation, and the supernatant containing the TFPI-3 was loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN. Inc., supra). Briefly the supernatant was loaded onto the column in 6 M guanidine-HCl, pH 8, the column was first washed with 10 volumes of 6 M guanidine-HCl, pH 8, then washed with 10 volumes of 6 M guanidine-HCl pH 6, and finally the TFPI-3 species were eluted with 6 M guanidine-HCl, pH 5 or pH 2.

The purified proteins were then renatured by dialyzing against phosphate-buffered saline (PBS) or 50 mM Na-acetate, pH 5 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 2

Cloning and Expression of TFPI-3 protein in a Baculovirus Expression System

In this example, the plasmid shuttle vector pA2 GP was used to insert the cloned DNA encoding the Kunitz-type domains of the TFPI-3 protein, lacking its naturally associated secretory signal (leader) sequence, into a baculovirus for expression, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (19989).

The cDNA sequence encoding the Kunitz-type domains in the deposited clone, lacking the AUG initiation codon and the naturally associated leader sequence shown in FIGS. 1A and 1B, were amplified using PCR oligonucleotide primers corresponding to the 5' and 3' sequences of the gene. The 5' primer had the sequence 5' CCCC AGATCTCGAACGCAGCATCCACGACTTCTGC 3' (SEQ ID NO:24) containing the underlined BglII restriction enzyme site followed by 24 nucleotides of the sequence of the mature TFPI-3 protein shown in SEQ ID NO:2, beginning with the indicated N-terminus of the Kunitz-type domain containing form of the TFPI-3 protein. The 3' primer had the sequence 5 CCCC TCTAGATTAATTCTCCTGCTGGCCGGAAGCAGC 3' (SEQ ID NO:25) containing the underlined XbaI restriction site followed by an artificial complimentary stop codon, TTA, and 23 nucleotides complementary to the 3' coding sequence in FIGS. 1A and 1B. The resulting fragment encodes seven TFPI-3 amino acids amino to the first Kunitz-type domain and six amino acids carboxy terminal to the second Kunitz-type domain shown in FIGS. 1A and 1B.

The amplified fragment was isolated from a 1% agarose gel using a commercially available kit ("Geneclean," BIO 101 Inc., La Jolla, Calif.). The fragment then was digested with BglII and XbaI and again is purified on a 1% agarose gel.

The plasmid was digested with the restriction enzymes BglII and XbaI and dephosphorylated using calf intestinal phosphatase, using routine procedures known in the art. The DNA was then isolated from a 1% agarose gel using a commercially available kit ("Geneclean" BIO 101 Inc., La Jolla, Calif.).

Fragment and the dephosphorylated plasmid were ligated together with T4 DNA ligase. *E. coli* HB101 and XL-1 Blue (Statagene Cloning Systems, La Jolla, Calif.) cells were transformed with the ligation mixture and spread on culture plates. Bacteria were identified that contain the plasmid with the human TFPI-3 gene by digesting DNA from individual colonies using BglII and XbaI and then analyzing the digestion product by gel electrophoresis. The sequence of the cloned fragment was confirmed by DNA sequencing. This plasmid is designated herein pA2TFPI-3.

Five μg of the plasmid pA2TFPI-3 was co-transfected with 1.0 μg of a commercially available linearized baculovirus DNA ("BaculoGold™ baculovirus DNA", Pharmingen, San Diego, Calif.), using the lipofection method described by Feigner et al., *Proc. Natl. Acad. Sci. USA* 84: 7413–7417 (1987). One μg of BaculoGold™ virus DNA and 5 μg of the plasmid pA2TFPI-3 were mixed in a sterile well of a microtiter plate containing 50 μl of serum-free Grace's medium (Life Technologies Inc., Gaithersburg, Md.). Afterwards, 10 μl Lipofectin plus 90 μl Grace's medium were added, mixed and incubated for 15 minutes at room temperature. Then the transfection mixture was added drop-wise to St9 insect cells (ATCC CRL 1711) seeded in a 35 mm tissue culture plate with 1 ml Grace's medium without serum. The plate was then incubated for 5 hours at 27° C. The transfection solution was then removed from the plate and 1 ml of Grace's insect medium supplemented with 10% fetal calf serum was added. Cultivation was then continued at 27° C. for four days.

After four days the supernatant was collected and a plaque assay is performed, as described by Summers and Smith, supra. An agarose gel with "Blue Gal" (Life Technologies Inc., Gaithersburg) was used to allow easy identification and isolation of gal-expressing clones, which produced blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques were picked with the tip of a micropipettor (e.g., Eppendorf). The agar containing the recombinant viruses was then resuspended in a microcentrifuge tube containing 200 µl of Grace's medium and the suspension containing the recombinant baculovirus was used to infect Sf9 cells seeded in 35 mm dishes. Four days later the supernatants of these culture dishes were harvested and then they are stored at 4° C. The recombinant virus is called V-TFPI-3.

To verify the expression of the TFPI-3 gene Sf9 cells were grown in Grace's medium supplemented with 10% heat-inactivated FBS. The cells were infected with the recombinant baculovirus V-TFPI-3 at a multiplicity of infection ("MOI") of about 2. The proteins in the supernatant as well as the intracellular proteins were analyzed by SDS-PAGE.

Example 3

Cloning and Expression of TFPI-3 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC37152), pSV2dhfr (ATCC 37146) and pBC12MI (ATCC67109). Mammalian host cells that could be used include, human Hela, 293, H9 and Jurkat cells, mouse NIH3T3 and C127 cells, Cos 1, Cos 7 and CVI, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid in this illustrative example, pTFPI-3HA, is made by cloning the cDNA encoding the complete TFPI-3 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete TFPI-3 polypeptide is cloned into the polylinker region of the vector so that recombinant protein expression is directed by the CMV promoter. The plasmid construction strategy is as follows. The TFPI-3 cDNA of the deposited clone is amplified using primers that contain convenient restriction sites, much as described above for construction of vectors for expression of TFPI-3 in *E. coli*. Suitable primers include the following, which are used in this example. The 5' primer, containing the underlined BglII site, a Kozak sequence, an AUG start codon, and 5' coding region of the complete TFPI-3 polypeptide, has the following sequence:

5' CCCC AGATCTGCCATCATGGCGCAGCTGTGCGGG CTGA 3' (SEQ ID NO:26). The 3' primer, containing the underlined XbaI restriction site has the following sequence: 5' CGC TCTAGATCACAGGACATATGTGTTCTT 3' (SEQ ID NO:27).

The PCR amplified DNA fragment and the vector, pcDNAI/Amp, are digested with BglII and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete TFPI-3 polypeptide.

For expression of recombinant TFPI-3, COS cells are transfected with an expression vector, as described above, using DEAE-DEXTRAN, as described. for instance, in Sambrook et al., *Molecular Cloning: a Laboratory Manual*, Cold Spring Laboratory Press, Cold Spring Harbor, N.Y. (1989). Cells are incubated under conditions for expression of TFPI-3 by the vector.

Expression of the TFPI-3-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TFPI-3 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol Chem.* 253:1357–1370, Hamlin, J. L. and Ma, C. 1990, *Biochem. et Biophys. Acta.* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TFPI-3 polypeptide in a regulated way in mammalian cells (Gossen, M., & Bujard, H. 1992, *Proc. Natl. Acad Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BglII and XbaI and then dephosphorylated using calf intestinal phosphates by procedures known in the art. The vector is then isolated from a 1% agarose gel.

The DNA sequence encoding the complete TFPI-3 polypeptide is amplified using PCR oligonucleotide primers corresponding to the 5' and 3' sequences of the desired portion of the gene. The 5' primer containing the underlined BglII site, a Kozak sequence, and an AUG start codon, has the following sequence:

5' CCCC AGATCTGCCATCATGGCGCAGCTGTTGCGG CTGA 3' (SEQ ID NO:26). The 3' primer, containing the underlined XbaI restriction site, has the following sequence: 5' CGC TCTAGATCACAGGACATATGTGTTCTT 3' (SEQ ID NO:27).

The amplified fragment is digested with the endonucleases BglII and XbaI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five pg of the expression plasmid pC4 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 4

Tissue distribution of TFPI-3 mRNA expression

Northern blot analysis was carried out to examine TFPI-3 gene expression in human tissues, including spleen, thymus, small intestine, colon, peripheral blood leukocytes, prostate and testis,. using methods described by, among others, Sambrook et al., cited above. A cDNA probe containing the entire nucleotide sequence of the TFPI-3 protein (SEQ ID NO:1) was labeled with $^{32}$P using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe was then used to examine various human tissues for TFPI-3 mRNA.

Multiple Tissue Northern (MTN) blots containing various human tissues (H) or human immune system tissues (IM) were obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Expression of TFPI-3 was observed in all tissues tested, but was highest in prostate and testis.

Example 5

TFPI-3 Trypsin Inhibition Assay

The expression, purification, and renaturation of the first Kunitz-type domain of the TFPI-3 protein (TFPI3-1) in *E. coli* is described in Example 1. The refolded samples were centrifuged at 15,000 g for 10 minutes to remove insoluble material. The purified protein was found to be more than 90% pure as observed by SDS-PAGE. The concentration of the protein was 1 mg/ml as measured by the Bradford assay.

The assay described in this example involves the use of p-toluenesulphonyl-L-arginine methyl ester (TAME) as a substrate for trypsin and was first described by Hummel, B.C.W. (Can J. Biochem. Physil., 37:1393 (1959)). Lyophilized aliquots of TAME (0.001 M TAME and 0.01 M calcium in 0.04 M Tris buffer, ph7.8 to 8.2, when reconstituted according to manufacturer's suggested protocol) were purchased from Worthington Biochemical Corporation (Freehold. N.J.). Trypsin (Sigma) was prepared in 50 mM Tris buffer, pH 8.0, at a concentration of 10 mg/ml. Ten ml trypsin was added to acetate buffer (50 mM Na-acetate, pH5.0, 200 mM NaCl) containing 1.25 ug, 2.50 ug, 5.0 ug, 10.0 ug and 20.0 ug of purified first Kunitz domain, in total volume of 100 ml. and incubated for 10 minutes at room temperature. After incubation, the samples were added to 1 ml of TAME reagent and absorbance at 247 nm was monitored at 37° C. in a period of 30 min according to Worthington's protocol. His-tagged Cripto (a TGF-a family member), purified in the same way as TFPI-3-1, was used as a negative control.

Results

Figure 4:
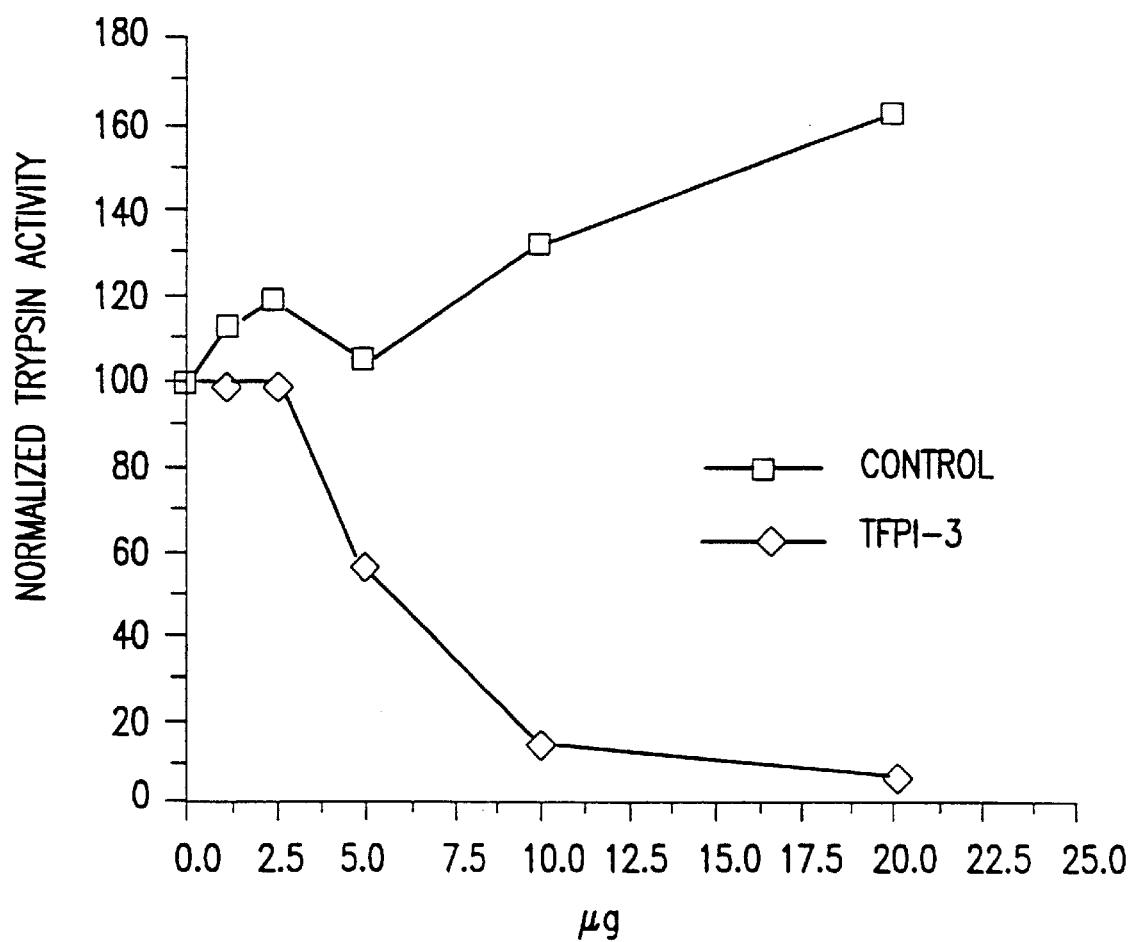
FIG. 4 shows the results of the trypsin inhibition assay described in Example 5. The error bar represent standard deviation (n=4). TFPI-3-1 refers to the first Kunitz-type domain of TFPI-3.

The results are shown in FIG. 4. As can be seen, TFPI-3-1 (first Kunitz type domain of TFPI-3) did not appear to inhibit trypsin activity at 1.25 and 2.50 mg doses. When 5.00 mg of TFPI-3-1 was included, approximately 60% of trypsin activity was inhibited. At 10.00 mg, trypsin activity was reduced to 13% as compared to the buffer-only control. Trypsin activity was almost totally abolished at 20.00 mg of TFPI-3-1. When the same concentrations of Cripto were used as a control no trypsin inhibiting activity could be observed.

The trypsin inhibiting activity of TFPI-3-1 was further confirmed by assaying duplicate samples in a single experiment. Trypsin (100 ng) was incubated with buffer only, 10 mg of Cripto or 10 mg of TFPI-3-1. After the addition of TAME substrate and absorbance at 247 nm was measured. Approximately 7% of trypsin activity was left in the TFPI-3-1 samples as compared to the buffer only samples (Table 2, below).

Table 2

Effects of TFPI-3-1 and Cripto Control on Inhibition of Trypsin Activity

TABLE 2

Effects of TFPI-3-1 and Cripto control on inhibition of trypsin activity.

| Buffer only | TFPI-3-1 (10 µg) | Cripto Control (10 µg) |
|---|---|---|
| 85 ± 3.5 | 6 ± 8.5 | 105 ± 0.7 |

Numbers Denote Trypsin Activity ($10^{-4}$* ΔA/min), n=2.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method for measuring the amount of TFPI-3 in a sample, comprising contacting said sample to an antibody or fragment thereof with specificity for a polypeptide consisting of amino acids 106 to 156 of SEQ ID NO:2, and assaying for binding of said antibody or fragment thereof.

2. The method of claim 1, wherein the amount of TFPI-3 in said sample is qualitatively compared to a standard amount of TFPI-3.

3. The method of claim 1, wherein the amount of TFPI-3 in said sample is quantitatively measured.

4. The method of claim 1, wherein said antibody or fragment thereof is labeled.

5. The method of claim 4, wherein the label is selected from the group consisting of:

(a) an enzyme;

(b) a fluorescent label;

(c) radioisotope;

(d) a radio-opaque label; and (e) a material detectable by nuclear magnetic resonance.

6. The method of claim 5, wherein said label is (a).

7. The method of claim 5, wherein said label is (b).

8. The method of claim 5, wherein said label is (c).

9. The method of claim 5, wherein said label is (d).

10. The method of claim 5, wherein said label is (e).

11. The method of claim 1, wherein said assaying comprises a technique selected from the group consisting of immunohistology, immunoassay, and in vivo imaging.

12. The method of claim 11, wherein said technique is an immunoassay.

13. The method of claim 12, wherein said immunoassay is an enzyme linked immunosorbent assay.

14. The method of claim 12, wherein said immunoassay is a radioimmunoassay.

15. The method of claim 12, wherein said immunoassay is western blotting.

16. The method of claim 11, wherein said technique is in vivo imaging.

17. The method of claim 16, wherein said in vivo imaging technique is X-radiography.

18. The method of claim 16, wherein said in vivo imaging technique is nuclear magnetic resonance (NMR).

19. The method of claim 16, wherein said in vivo imaging technique is electron spin resonance (ESR).

20. The method of claim 11, wherein said technique is immunohistology.

21. The method of claim 1, wherein said antibody or fragment thereof is polyclonal.

22. The method of claim 1, wherein said antibody or fragment thereof is monoclonal.

23. The method of claim 1, wherein said antibody or fragment thereof is chimeric.

24. The method of claim 1, wherein said antibody or fragment thereof is produced by hybridoma technology.

25. The method of claim 1, wherein said antibody or fragment thereof is produced through recombinant DNA technology.

26. The method of claim 1, wherein said sample is selected from the group consisting of serum, plasma, urine, synovial fluid, spinal fluid, and a tissue biopsy.

27. The method of claim 26, wherein said sample is serum.

28. The method of claim 26, wherein said sample is plasma.

29. The method of claim 26, wherein said sample is urine.

30. The method of claim 26, wherein said sample is synovial fluid.

31. The method of claim 26, wherein said sample is spinal fluid.

32. The method of claim 26, wherein said sample is a tissue biopsy.

* * * * *